United States Patent
Caffrey et al.

(10) Patent No.: US 7,495,013 B2
(45) Date of Patent: Feb. 24, 2009

(54) CHEMICAL COMPOUNDS

(75) Inventors: Moya Caffrey, Loughborough (GB); Christopher Luckhurst, Loughborough (GB); Tobias Mochel, Loughborough (GB); Matthew Perry, Loughborough (GB); Brian Springthorpe, Loughborough (GB)

(73) Assignee: AstraZeneca AB (SE)

( * ) Notice: Subject to any disclaimer, the term of this patent is extended or adjusted under 35 U.S.C. 154(b) by 530 days.

(21) Appl. No.: 10/551,493

(22) PCT Filed: Mar. 30, 2004

(86) PCT No.: PCT/SE2004/000489

§ 371 (c)(1), (2), (4) Date: Sep. 29, 2005

(87) PCT Pub. No.: WO2004/087659

PCT Pub. Date: Oct. 14, 2004

(65) Prior Publication Data

US 2007/0032523 A1    Feb. 8, 2007

(51) Int. Cl.
A61K 31/4545    (2006.01)
C07D 401/06    (2006.01)

(52) U.S. Cl. .................... 514/316; 546/188; 546/187; 546/190

(58) Field of Classification Search ............... 514/316; 546/188, 187, 190
See application file for complete search history.

(56) References Cited

U.S. PATENT DOCUMENTS

| | | | |
|---|---|---|---|
| 4,505,915 A | 3/1985 | Hannah | |
| 4,588,722 A | 5/1986 | Janssens et al. | |
| 4,695,575 A | 9/1987 | Janssens et al. | |
| 5,883,096 A | 3/1999 | Lowe et al. | |
| 5,889,006 A | 3/1999 | Lowe et al. | |
| 5,952,349 A | 9/1999 | Asberom et al. | |
| 5,977,138 A | 11/1999 | Wang et al. | |
| 6,066,636 A | 5/2000 | Kozlowski et al. | |
| 6,294,554 B1 | 9/2001 | Clader et al. | |
| 6,387,930 B1 | 5/2002 | Baroudy et al. | |
| 6,440,440 B1 | 8/2002 | Meerpoel et al. | |
| 6,525,070 B2 | 2/2003 | Rigby et al. | |
| 6,759,411 B2 | 7/2004 | Ko et al. | |
| 6,903,115 B2 | 6/2005 | Rigby et al. | |
| 7,179,922 B2 | 2/2007 | Lawrence et al. | |
| 7,186,718 B2 | 3/2007 | Gustafsson et al. | |
| 7,238,691 B2 | 7/2007 | Sanganee et al. | |
| 7,238,811 B2 | 7/2007 | Lawrence et al. | |
| 7,265,227 B2 | 9/2007 | Evans et al. | |
| 7,307,090 B2 | 12/2007 | Evans et al. | |
| 2005/0176708 A1 | 8/2005 | Luckhurst et al. | |
| 2005/0182094 A1 | 8/2005 | Sanganee et al. | |
| 2006/0040984 A1 | 2/2006 | Luckhurst et al. | |
| 2006/0264463 A1 | 11/2006 | Luckhurst et al. | |
| 2006/0281726 A1 | 12/2006 | Luckhurst et al. | |
| 2007/0179297 A1 | 8/2007 | Lawrence et al. | |

FOREIGN PATENT DOCUMENTS

| | | |
|---|---|---|
| EP | 0 099 139 | 1/1984 |
| EP | 0 121 972 | 10/1984 |
| EP | 0 145 037 | 6/1985 |
| EP | 0 151 824 | 8/1985 |
| EP | 0 151 826 | 8/1985 |
| EP | 1 076 055 | 2/2001 |
| EP | 1 362 857 | 11/2003 |
| EP | 1 389 616 | 2/2004 |
| GB | 1250719 | 10/1971 |
| GB | 2 373 186 | 9/2002 |
| WO | WO 93/10091 | 5/1993 |
| WO | WO 95/08535 | 3/1995 |
| WO | WO 96/26196 | 8/1996 |
| WO | WO 96/34857 | 11/1996 |
| WO | WO 96/41631 | 12/1996 |
| WO | WO 97/24324 | 7/1997 |
| WO | WO 98/01425 | 1/1998 |
| WO | WO 98/05291 | 2/1998 |
| WO | WO 98/05292 | 2/1998 |
| WO | WO 98/06697 | 2/1998 |
| WO | WO 98/11128 | 3/1998 |
| WO | WO 99/04794 | 2/1999 |
| WO | WO 99/37304 | 7/1999 |
| WO | WO 99/38514 | 8/1999 |
| WO | WO 99/51578 | 10/1999 |
| WO | WO 99/55324 | 11/1999 |

(Continued)

OTHER PUBLICATIONS

Harada et al., "Novel N-[1-(Substituted 4-Piperidinylmethyl)-4-piperidinyl]benzamides as Potent Colonic Prokinetic Agents", *Bioorganic & Medicinal Chemistry Letters* 12:967-970 (2002).

(Continued)

*Primary Examiner*—Charanjit S Aulakh
(74) *Attorney, Agent, or Firm*—Fish & Richardson P.C.

(57) ABSTRACT

The present invention relates to compounds of formula (I):

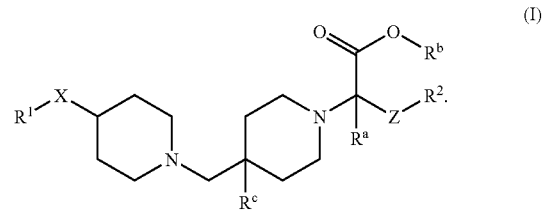

The variables recited in formula (I) are defined in the specification. The present invention also relates to processes of preparing compounds of formula (I) and uses of such compounds for treating a chemokine (e.g., CCR3) or H1 mediated disease state.

19 Claims, No Drawings

FOREIGN PATENT DOCUMENTS

| | | |
|---|---|---|
| WO | WO 00/00488 | 1/2000 |
| WO | WO 00/12478 | 3/2000 |
| WO | WO 00/32590 | 6/2000 |
| WO | WO 00/35877 | 6/2000 |
| WO | WO 00/66559 | 11/2000 |
| WO | WO 01/02381 | 1/2001 |
| WO | WO 01/07436 | 2/2001 |
| WO | WO 01/29066 | 4/2001 |
| WO | WO 01/77101 | 10/2001 |
| WO | WO 01/92227 | 12/2001 |
| WO | WO 02/18335 | 3/2002 |
| WO | WO 02/20484 | 3/2002 |
| WO | WO 02/072570 | 3/2002 |
| WO | WO 02/066460 | 8/2002 |
| WO | WO 02/079190 | 10/2002 |
| WO | WO 02/079194 | 10/2002 |
| WO | WO 02/081449 | 10/2002 |
| WO | WO 03/004487 | 1/2003 |
| WO | WO 03/018576 | 3/2003 |
| WO | WO 03/020716 | 3/2003 |
| WO | WO 03/022277 | 3/2003 |
| WO | WO 03/024962 | 3/2003 |
| WO | WO 03/078395 | 9/2003 |
| WO | WO 03/078421 | 9/2003 |
| WO | WO 2005/126947 | 11/2003 |
| WO | WO 2004/029041 | 4/2004 |
| WO | WO 2004/085423 | 10/2004 |
| WO | WO 2004/099144 | 11/2004 |
| WO | WO 2004/113323 | 12/2004 |
| WO | WO 2005/097775 | 10/2005 |
| WO | WO 2006/126948 | 11/2006 |
| WO | WO 2007/011293 | 1/2007 |

OTHER PUBLICATIONS

Hodgson et al., "Chemokines and Drug Discovery", *Drug New Perspect* 17(5):335-338 (2004).

Hoffman et al., "The Preparation of 2-Hydrazinyl Esters in High Optical Purity from 2-Sulfonyloxy Esters", *Tetrahedron Letters* 31(21):2953-2956 (1990).

Allain et al., (2005) STN International, HCAPLUS Database, Columbus, OH, Accession No. 1992:187881, Reg. No. 46817-91-8, citing "Antidepressants and cognition: comparative effects of moclobemide, viloxazine and maprotiline", *psychopharmacology* 106 (Suppl.).

Cohen et al., *Am. J. Clin. Pathol.* 105:589 (1996).

Hermans et al., "4-Substituted Piperidines. II. Reaction of 1-Benzyl-4-cyano-4-t-aminopiperidines with Organometallic Compounds", *J. Med. Chem.* 8(6):851-855 (1965) at p. 852 ("compound 12" in Table I).

Patani and LaVoie, "Bioisosterism: A Rational Approach in Drug Design", *Chem. Rev.* 96:3147-3176 (1996).

STN International, File CAPLUS, CAPLUS accession No. 1988:630911, Document No. 109:230911, Lehmann, Jochen et al: "Lactones. XVIII. Synthesis of lactone-bridged 1,1-diarylpropanamines"; & *Arch. Pharm.* (Weinheim, Ger.) (1988), 321(7), 443-445.

Machii et al., "Preparation of 5-cyanopyrimidine derivatives as anti-inflammatory agents", CAPLUS 139:307788 (2003).

Mattson et al., "Preparation of [(oxopyrolidinylmethyl)piperidinyl]pyrimidines as nootropics and memory enhancers", CAPLUS 116:151786 (1992).

CHEMICAL COMPOUNDS

CROSS-REFERENCE TO RELATED APPLICATIONS

This application is a national phase application under 35 U.S.C. § 371 of PCT International Application No. PCT/SE2004/000489, filed Mar. 30, 2004, which claims priority to Swedish Application Ser. No. 0300957-8, filed Apr. 1, 2003.

The present invention concerns piperidine derivatives having pharmaceutical activity, to processes for preparing such derivatives, to pharmaceutical compositions a comprising such derivatives and to the use of such derivatives as active therapeutic agents.

Pharmaceutically active piperidine derivatives are disclosed in WO99/38514, WO99/04794 and WO00/35877.

Histamine is a basic amine, 2-(4-imidazolyl)-ethylamine, and is formed from histidine by histidine decarboxylase. It is found in most tissues of the body, but is present in high concentrations in the lung, skin and in the gastrointestinal tract. At the cellular level inflammatory cells such as mast cells and basophils store large amounts of histamine. It is recognised that the degranulation of mast cells and basophils and the subsequent release of histamine is a fundamental mechanism responsible for the clinical manifestation of an allergic process. Histamine produces its actions by an effect on specific histamine G-protein coupled receptors, which are of three main types, H1, H2 and H3. Histamine H1 antagonists comprise the largest class of medications used in the treatment of patients with allergic disorders, for example rhinitis or urticaria. H1 antagonists are useful in controlling the allergic response by for example blocking the action of histamine on post-capillary venule smooth muscle, resulting in decreased vascular permeability, exudation and oedema. The antagonists also produce blockade of the actions of histamine on the H1 receptors on c-type nociceptive nerve fibres, resulting in decreased itching and sneezing.

Chemokines are chemotactic cytokines that are released by a wide variety of cells to attract macrophages, T cells, eosinophils, basophils and neutrophils to sites of inflammation and also play a rôle in the maturation of cells of the immune system. Chemokines play an important rôle in immune and inflammatory responses in various diseases and disorders, including asthma and allergic diseases, as well as autoimmune pathologies such as rheumatoid arthritis and atherosclerosis. These small secreted molecules are a growing superfamily of 8-14 kDa proteins characterised by a conserved four cysteine motif. The chemokine superfamily can be divided into two main groups exhibiting characteristic structural motifs, the Cys-X-Cys (C-X-C, or α) and Cys-Cys (C-C, or β) families. These are distinguished on the basis of a single amino acid insertion between the NH-proximal pair of cysteine residues and sequence similarity.

The C-X-C chemokines include several potent chemoattractants and activators of neutrophils such as interleukin-8 (IL-8) and neutrophil-activating peptide 2 (NAP-2).

The C-C chemokines include potent chemoattractants of monocytes and lymphocytes but not neutrophils such as human monocyte chemotactic proteins 1-3 (MCP-1, MCP-2 and MCP-3), RANTES (Regulated on Activation, Normal T Expressed and Secreted), eotaxin and the macrophage inflammatory proteins 1α and 1β (MIP-1α and MIP-1β).

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10, CXCR1, CXCR2, CXCR3 and CXCR4. These receptors represent good targets for drug development since agents which modulate these receptors would be useful in the treatment of disorders and diseases such as those mentioned above.

Viral infections are known to cause lung inflammation. It has been shown experimentally that the common cold increases mucosal output of eotaxin in the airways. Instillation of eotaxin into the nose can mimic some of the signs and symptoms of a common cold. (See, Greiff L et al Allergy (1999) 54(11) 1204-8 [Experimental common cold increase mucosal output of eotaxin in atopic individuals] and Kawaguchi M et al Int. Arch. Allergy Immunol. (2000) 122 S1 44 [Expression of eotaxin by normal airway epithelial cells after virus A infection].)

The present invention provides a compound of formula (I):

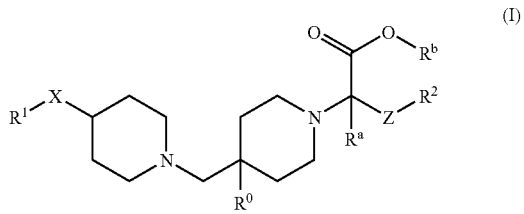

wherein:
$R^a$ and $R^b$ are, independently, hydrogen or $C_{1-4}$ alkyl or $R^a$ forms part of a ring as defined below;
$R^c$ is hydrogen or hydroxy;
X is $CH_2$, C(O), O, S, S(O), S(O)$_2$ or $NR^3$;
Z is $CHR^d(CH_2)_n$;
n is 0 or 1;
$R^d$ is hydrogen, $C_{1-4}$ alkyl, hydroxy or $C_{1-4}$ alkoxy;
$R^1$ is hydrogen, $C_{1-6}$ alkyl, aryl or heterocyclyl;
$R^2$ is aryl or heterocyclyl;
wherein, unless stated otherwise, the foregoing aryl and heterocyclyl moieties are optionally substituted by: halogen, cyano, nitro, hydroxy, oxo, $S(O)_pR^4$, $OC(O)NR^5R^6$, $NR^7R^8$, $NR^9C(O)R^{10}$, $NR^{11}C(O)NR^{12}R^{13}$, $S(O)_2NR^{14}R^{15}$, $NR^{16}S(O)_2R^{17}$, $C(O)NR^{18}R^{19}$, $C(O)R^{20}$, $CO_2R^{21}$, $NR^{22}CO_2R^{23}$, $C_{1-6}$ alkyl, $CF_3$, $C_{1-6}$ alkoxy($C_{1-6}$)alkyl, $C_{1-6}$ alkoxy, $OCF_3$, $C_{1-6}$ alkoxy($C_{1-6}$)alkoxy, $C_{1-6}$ alkylthio, $C_{2-6}$ alkenyl, $C_{2-6}$ alkynyl, $C_{3-10}$ cycloalkyl (itself optionally substituted by $C_{1-4}$ alkyl or oxo), methylenedioxy, difluoromethylenedioxy, phenyl, phenyl($C_{1-4}$) alkyl, phenoxy, phenylthio, phenyl($C_{1-4}$)alkoxy, heterocyclyl, heterocyclyl($C_{1-4}$)alkyl, heterocyclyloxy or heterocyclyl($C_{1-4}$)alkoxy; wherein any of the immediately foregoing phenyl and heterocyclyl moieties are optionally substituted with halogen, hydroxy, nitro, $S(O)_q(C_{1-4}$ alkyl), $S(O)_2NH_2$, $S(O)_2NH(C_{1-4}$ alkyl), $S(O)_2N(C_{1-4}$ alkyl)$_2$ (and these alkyl groups may join to form a ring as described for $R^5$ and $R^6$ below), cyano, $C_{1-4}$ alkyl, $C_{1-4}$ alkoxy, C(O)$NH_2$, C(O)NH($C_{1-4}$ alkyl), C(O)N($C_{1-4}$ alkyl)$_2$ (and these alkyl groups may join to form a ring as described for $R^5$ and $R^6$ below), $CO_2H$, $CO_2(C_{1-4}$ alkyl), NHC(O)($C_{1-4}$ alkyl), NHS(O)$_2(C_{1-4}$ alkyl), C(O)($C_{1-4}$ alkyl), $CF_3$ or $OCF_3$; or Z, $R^2$ and $R^a$ together with the carbon atom to which Z and $R^a$ are attached form a ring; p and q are, independently, 0, 1 or 2;
$R^5, R^6, R^7, R^8, R^9, R^{10}, R^{11}, R^{12}, R^{13}, R^{14}, R^{15}, R^{16}, R^{18}, R^{19}, R^{20}, R^{21}$ and $R^{22}$ are, independently, hydrogen, $C_{1-6}$ alkyl (optionally substituted by halogen, hydroxy or $C_{3-10}$ cycloalkyl), $CH_2(C_{2-6}$ alkenyl), phenyl (itself optionally substituted by halogen, hydroxy, nitro, $NH_2$, $NH(C_{1-4}$ alkyl), N(C$_{1-4}$ alkyl)$_2$ (and these alkyl groups may join to form a ring as described for R$^5$ and R$^6$ below), S(O)$_2$(C$_{1-4}$ alkyl), S(O)$_2$NH$_2$, S(O)$_2$NH(C$_{1-4}$ alkyl), S(O)$_2$N(C$_{1-4}$ alkyl)$_2$ (and these alkyl groups may join to form a ring as described for R$^5$ and R$^6$ below), cyano, C$_{1-4}$ alkyl, C$_{1-4}$ alkoxy, C(O)NH$_2$, C(O)NH(C$_{1-4}$ alkyl), C(O)N(C$_{1-4}$ alkyl)$_2$ (and these alkyl groups may join to form a ring as described for R$^5$ and R$^6$ below), CO$_2$H, CO$_2$(C$_{1-4}$ alkyl), NHC(O)(C$_{1-4}$ alkyl), NHS(O)$_2$(C$_{1-4}$ alkyl), C(O)(C$_{1-4}$ alkyl), CF$_3$ or OCF$_3$) or heterocyclyl (itself optionally substituted by halogen, hydroxy, nitro, NH$_2$, NH(C$_{1-4}$ alkyl), N(C$_{1-4}$ alkyl)$_2$ (and these alkyl groups may join to form a ring as described for R$^5$ and R$^6$ below), S(O)$_2$(C$_{1-4}$ alkyl), S(O)$_2$NH$_2$, S(O)$_2$NH(C$_{1-4}$ alkyl), S(O)$_2$N(C$_{1-4}$ alkyl)$_2$ (and these alkyl groups may join to form a ring as described for R$^5$ and R$^6$ below), cyano, C$_{1-4}$ alkyl, C$_{1-4}$ alkoxy, C(O)NH$_2$, C(O)NH(C$_{1-4}$ alkyl), C(O)N(C$_{1-4}$ alkyl)$_2$ (and these alkyl groups may join to form a ring as described for R$^5$ and R$^6$ below), CO$_2$H, CO$_2$(C$_{1-4}$alkyl), NHC(O)(C$_{1-4}$ alkyl), NHS(O)$_2$(C$_{1-4}$ alkyl), C(O)(C$_{1-4}$ alkyl), CF$_3$ or OCF$_3$);

alternatively NR$^5$R$^6$, NR$^7$R$^8$, NR$^{12}$R$^{13}$, NR$^{14}$R$^{15}$, NR$^{18}$R$^{19}$, may, independently form a 4-7 membered heterocyclic ring, azetidine, pyrrolidine, piperidine, azepine, morpholine or piperazine, the latter optionally substituted by C$_{1-4}$ alkyl on the distal nitrogen;

R$^4$, R$^{17}$ and R$^{23}$ are, independently, C$_{1-6}$ alkyl (optionally substituted by halogen, hydroxy or C$_{3-10}$ cycloalkyl), CH$_2$(C$_{2-6}$ alkenyl), phenyl (itself optionally substituted by halogen, hydroxy, nitro, NH$_2$, NH(C$_{1-4}$ alkyl), N(C$_{1-4}$ alkyl)$_2$ (and these alkyl groups may join to form a ring as described for R$^5$ and R$^6$ above), S(O)$_2$(C$_{1-4}$ alkyl), S(O)$_2$NH$_2$, S(O)$_2$NH(C$_{1-4}$ alkyl), S(O)$_2$N(C$_{1-4}$ alkyl)$_2$ (and these alkyl groups may join to form a ring as described for R$^5$ and R$^6$ above), cyano, C$_{1-4}$ alkyl, C$_{1-4}$ alkoxy, C(O)NH$_2$, C(O)NH(C$_{1-4}$ alkyl), C(O)N(C$_{1-4}$ alkyl)$_2$ (and these alkyl groups may join to form a ring as described for R$^5$ and R$^6$ above), CO$_2$H, CO$_2$(C$_{1-4}$ alkyl), NHC(O)(C$_{1-4}$ alkyl), NHS(O)$_2$(C$_{1-4}$ alkyl), C(O)(C$_{1-4}$ alkyl), CF$_3$ or OCF$_3$) or heterocyclyl (itself optionally substituted by halogen, hydroxy, nitro, NH$_2$, NH(C$_{1-4}$ alkyl), N(C$_{1-4}$ alkyl)$_2$ (and these alkyl groups may join to form a ring as described for R$^5$ and R$^6$ above), S(O)$_2$(C$_{1-4}$ alkyl), S(O)$_2$NH$_2$, S(O)$_2$NH(C$_{1-4}$ alkyl), S(O)$_2$N(C$_{1-4}$ alkyl)$_2$ (and these alkyl groups may join to form a ring as described for R$^5$ and R$^6$ above), cyano, C$_{1-4}$ alkyl, C$_{1-4}$ alkoxy, C(O)NH$_2$, C(O)NH(C$_{1-4}$ alkyl), C(O)N(C$_{1-4}$ alkyl)$_2$ (and these alkyl groups may join to form a ring as described for R$^5$ and R$^6$ above), CO$_2$H, CO$_2$(C$_{1-4}$ alkyl), NHC(O)(C$_{1-4}$ alkyl), NHS(O)$_2$(C$_{1-4}$ alkyl), C(O)(C$_{1-4}$ alkyl), CF$_3$ or OCF$_3$);

R$^3$ is hydrogen, C$_{1-6}$ alkyl or benzyl;

or an N-oxide thereof; or a pharmaceutically acceptable salt thereof; or a solvate thereof.

Certain compounds of the present invention can exist in different isomeric forms (such as enantiomers, diastereomers, geometric isomers or tautomers). The present invention covers all such isomers and mixtures thereof in all proportions.

Suitable salts include acid addition salts such as a hydrochloride, dihydrochloride, hydrobromide, phosphate, sulfate, acetate, diacetate, fumarate, maleate, tartrate, citrate, oxalate, methanesulfonate or p-toluenesulfonate.

The compounds of the invention may exist as solvates (such as hydrates) and the present invention covers all such solvates.

Halogen includes fluorine, chlorine, bromine and iodine. Halogen is, for example, fluorine or chlorine.

Alkyl groups and moieties are straight or branched chain and comprise, for example, 1 to 6 (such as 1 to 4) carbon atoms. Examples of alkyl groups are methyl, ethyl, n-propyl, iso-propyl or tert-butyl.

Alkyl optionally substituted by halogen and haloalkyl comprise an alkyl part and one or more (for example 1 to 6) of the same or different halogen atoms. Alkyl optionally substituted by halogen and haloalkyl are, for example, CF$_3$.

Alkenyl and alkynyl groups comprise, for example, 2 to 6 (such as 2 to 4) carbon atoms. Examples of alkenyl groups are vinyl or allyl; and an example of an alkynyl group is propargyl.

Aryl includes phenyl and naphthyl and in one embodiment of the invention is, for example, phenyl.

In one embodiment cycloalkyl groups comprise from 3 to 10 (such as 3 to 8, for example 3 to 6) carbon atoms and are mono-, bi or tricyclic. Cycloalkyl is, for example, cyclopropyl, cyclopentyl, cyclohexyl, norbornyl or camphoryl. The cycloalkyl ring is optionally fused to a benzene ring (for example forming a bicyclo[4.2.0]octa-1,3,5-trienyl or indanyl ring system). In a further embodiment cycloalkyl is monocyclic.

Heterocyclyl is an aromatic or non-aromatic 5 or 6 membered ring, optionally fused to one or more other rings, comprising at least one heteroatom selected from the group comprising nitrogen, oxygen and sulfur; or an N-oxide thereof, or an S-oxide or S-dioxide thereof. Heterocyclyl is, for example, furyl, thienyl (also known as thiophenyl), pyrrolyl, 2,5dihydropyrrolyl, thiazolyl, pyrazolyl, oxazolyl, isoxazolyl, imidazolyl, piperidinyl, morpholinyl, pyridinyl, dihydropyridinyl (for example in a 6-oxo-1,6-dihydro-pyridinyl moiety), pyrimidinyl, indolyl, 2,3-dihydroindolyl, benzo[b]furyl (also known as benzfuryl), benz[b]thienyl (also known as benzthienyl or benzthiophenyl), 2,3-dihydrobenz[b]thienyl (for example in a 1-dioxo-2,3dihydrobenz[b]thienyl moiety), indazolyl, benzimidazolyl, benztriazolyl, benzoxazolyl, benzthiazolyl (for example in a 1H-benzthiazol-2-one-yl moiety), 2,3-dihydrobenzthiazolyl (for example in a 2,3-dihydrobenzthiazol-2-one-yl moiety), 1,2,3-benzothiadiazolyl, an imidazopyridinyl (such as imidazo[1,2a]pyridinyl), thieno[3,2-b]pyridin-6-yl, 1,2,3-benzoxadiazolyl, benzo[1,2,3]thiadiazolyl, 2,1,3-benzothiadiazolyl, benzofurazan (also known as 2,1,3-benzoxadiazolyl), quinoxalinyl, dihydro-1-benzopyryliumyl (for example in a coumarinyl or a chromonyl moiety), 3,4-dihydro-1H-2,1-benzothiazinyl (for example in a 2-dioxo-3,4dihydro-1H-2,1-benzothiazinyl moiety), a pyrazolopyridine (for example 1H-pyrazolo[3,4b]pyridinyl), a purine (for example in a 3,7-dihydro-purin-2,6-dione-8-yl moiety), quinolinyl, isoquinolinyl, dihydroisoquinolinyl (for example in a 2H-isoquinolin-1-one-yl moiety), a naphthydidinyl (for example [1,6]naphthyridinyl or [1,8]naphthyridinyl), a dihydro[1,8]naphthyridinyl (for example in a 1H-[1,8]naphthyridin4one-yl moiety)) a benzothiazinyl, a dihydrobenzothiazinyl (for example in a 4H-benzo[1,4]thiazin-3-one-yl moiety), benzo[d]imidazo[2,1-b]thiazol-2-yl or dibenzothiophenyl (also known as dibenzothienyl); or an N-oxide thereof, or an S-oxide or S-dioxide thereof.

An N-oxide of a compound of formula (I) is, for example, a 1-oxy-[1,4']bipiperidinyl-1'-yl compound.

In one particular aspect the invention provides a compound of formula (I) wherein R$^a$ and R$^b$ are, independently, hydrogen or C$_{1-4}$ alkyl or R$^a$ forms part of a ring as defined below; R$^c$ is hydrogen or hydroxy; X is CH$_2$, C(O), O, S, S(O), S(O)$_2$ or NR$^3$; Z is (CH$_2$)$_n$; n is 1 or 2; R$^1$ is hydrogen, C$_{1-6}$ alkyl, aryl or heterocyclyl; R$^2$ is aryl or heterocyclyl; wherein, unless stated otherwise, the foregoing aryl and heterocyclyl moieties are optionally substituted by: halogen, cyano, nitro, hydroxy, oxo, $S(O)_pR^4$, $OC(O)NR^5R^6$, $NR^7R^8$, $NR^9C(O)R^{10}$, $NR^{11}C(O)NR^{12}R^{13}$, $S(O)_2NR^{14}R^{15}$, $NR^{16}S(O)_2R^{17}$, $C(O)NR^{18}R^{19}$, $C(O)R^{20}$, $CO_2R^{21}$, $NR^{22}CO_2R^{23}$, $C_{1-6}$ alkyl, $CF_3$, $C_{1-6}$ alkoxy$(C_{1-6})$alkyl, $C_{1-6}$ alkoxy, $OCF_3$, $C_{1-6}$ alkoxy$(C_{1-6})$alkoxy, $C_{1-6}$ alkylthio, $C_{2-6}$ alkenyl, $C_{2-6}$ alkynyl, $C_{3-10}$ cycloalkyl (itself optionally substituted by $C_{1-4}$ alkyl or oxo), methylenedioxy, difluoromethylenedioxy, phenyl, phenyl$(C_{1-4})$alkyl, phenoxy, phenylthio, phenyl$(C_{1-4})$alkoxy, heterocyclyl, heterocyclyl$(C_{1-4})$alkyl, heterocyclyloxy or heterocyclyl$(C_{1-4})$alkoxy; wherein any of the immediately foregoing phenyl and heterocyclyl moieties are optionally substituted with halogen, hydroxy, nitro, $S(O)_q(C_{1-4}$ alkyl), $S(O)_2NH_2$, $S(O)_2NH(C_{1-4}$ alkyl), $S(O)_2N(C_{1-4}$ alkyl)$_2$ (and these alkyl groups may join to form a ring as described for $R^5$ and $R^6$ below), cyano, $C_{1-4}$ alkyl, $C_{1-4}$ alkoxy, $C(O)NH_2$, $C(O)NH(C_{1-4}$ alkyl), $C(O)N(C_{1-4}$alkyl)$_2$ (and these alkyl groups may join to form a ring as described for $R^5$ and R6 below), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$; or Z, $R^2$ and $R^a$ together with the carbon atom to which Z and $R^a$ are attached form a ring; p and q are, independently, 0, 1 or 2; $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{18}$, $R^{19}$, $R^{20}$, $R^{21}$ and $R^{22}$ are, independently, hydrogen, $C_{1-6}$ alkyl (optionally substituted by halogen, hydroxy or $C_{3-10}$ cycloalkyl), $CH_2(C_{2-6}$ alkenyl), phenyl (itself optionally substituted by halogen, hydroxy, nitro, $NH_2$, $NH(C_{1-4}$ alkyl), $N(C_{1-4}$ alkyl)$_2$, $S(O)_2C_{1-4}$ alkyl), $S(O)_2NH_2$, $S(O)_2NH(C_{1-4}$ alkyl), $S(O)_2N(C_{1-4}$ alkyl)$_2$ (and these alkyl groups may join to form a ring as described for $R^5$ and $R^6$ below), cyano, $C_{1-4}$ alkyl, $C_{1-4}$ alkoxy, $C(O)NH_2$, $C(O)NH(C_{1-4}$-alkyl), $C(O)N(C_{1-4}$ alkyl)$_2$ (and these alkyl groups may join to form a ring as described for $R^5$ and $R^6$ below), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$) or heterocyclyl (itself optionally substituted by halogen, hydroxy, nitro, $NH_2$, $NH(C_{1-4}$ alkyl), $N(C_{1-4}$ alkyl)$_2$, $S(O)_2(C_{1-4}$ alkyl), $S(O)_2NH_2$, $S(O)_2NH(C_{1-4}$ alkyl), $S(O)_2N(C_{1-4}$ alkyl)$_2$ (and these alkyl groups may join to form a ling as described for $R^5$ and $R^6$ below), cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$ (and these alkyl groups may join to form a ring as described for $R^5$ and $R^6$ below), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$); alternatively $NR^5R^6$, $NR^7R^8$, $NR^{12}R^{13}$, $NR^{14}R^{15}$, $NR^{18}R^{19}$, may, independently, form a 4-7 membered heterocyclic ring, azetidine, pyrrolidine, piperidine, azepine, morpholine or piperazine, the latter optionally substituted by $C_{1-4}$ alkyl on the distal nitrogen; $R^4$, $R^{17}$ and $R^{23}$ are, independently, $C_{1-6}$ alkyl (optionally substituted by halogen, hydroxy or $C_{3-10}$ cycloalkyl), $CH_2(C_{2-6}$ alkenyl), phenyl (itself optionally substituted by halogen, hydroxy, nitro, $NH_2$, $NH(C_{1-4}$ alkyl), $N(C_{1-4}$ alkyl)$_2$ (and these alkyl groups may join to form a ring as described for $R^5$ and $R^6$ above), $S(O)_2(C_{1-4}$ alkyl), $S(O)_2NH_2$, $S(O)NH(C_{1-4}$ alkyl), $S(O)_2N(C_{1-4}$ alkyl)$_2$ (and these alkyl groups may join to form a ring as described for $R^5$ and $R^6$ above), cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$ (and these alkyl groups may join to form a ring as described for $R^5$ and $R^6$ above), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$) or heterocyclyl (itself optionally substituted by halogen, hydroxy, nitro, $NH_2$, $NH(C_{1-4}$ alkyl), $N(C_{1-4}$ alkyl)$_2$ (and these alkyl groups may join to form a ring as described for $R^5$ and $R^6$ above), $S(O)_2(C_{1-4}$ alkyl), $S(O)_2NH_2$, $S(O)_2NH(C_{1-4}$ alkyl), $S(O)_2N(C_{1-4}$ alkyl)$_2$ (and these alkyl groups may join to form a ring as described for $R^5$ and $R^6$ above), cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$ (and these alkyl groups may join to form a ring as described for $R^5$ and $R^6$ above), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$); $R^3$ is hydrogen, $C_{1-6}$ alkyl or benzyl; or an N-oxide thereof; or a pharmaceutically acceptable salt thereof; or a solvate thereof.

In a further aspect-the invention provides a compound of formula (I) wherein X is O.

In another aspect of the invention the foregoing aryl (for example phenyl) and heterocyclyl moieties of $R^1$ and $R^2$ are, independently, optionally substituted by: halogen, cyano, nitro, hydroxy, oxo, $S(O)_pR^4$, $OC(O)NR^5R^6$, $NR^7R^8$, $NR^9C(O)R^{10}$, $NR^{11}C(O)NR^{12}R^{13}$, $S(O)_2NR^{14}R^{15}$, $NR^{16}S(O)_2R^{17}$, $C(O)NR^{18}R^{19}$, $C(O)R^{20}$, $CO_2R^{21}$, $NR^{22}CO_2R^{23}$, $C_{1-6}$ alkyl, $CF_3$, $C_{1-6}$ alkoxy$(C_{1-6})$alkyl, $C_{1-6}$ alkoxy or $OCF_3$; p is 0, 1 or 2; $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{18}$, $R^{19}$, $R^{20}$, $R^{21}$ and $R^{22}$ are, independently, hydrogen, $C_{1-6}$ alkyl (optionally substituted by halogen) or phenyl (itself optionally substituted by halogen, hydroxy, nitro, $NH_2$, $NH(C_{1-4}$alkyl), $N(C_{1-4}$alkyl)$_2$, $S(O)_2(C_{1-4}$alkyl), $S(O)_2NH_2$, $S(O)_2NH(C_{1-4}$alkyl), $S(O)_2N(C_{1-4}$alkyl)$_2$, cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$, $CO_2H$, $CO_2(C_{1-4}$ alkyl), $NHC(O)(C_{1-4}$ alkyl), $NHS(O)_2(C_{1-4}$alkyl), $C(O)(C_{1-4}$alkyl), $CF_3$ or $OCF_3$); and $R^4$, $R^{17}$ and $R^{23}$ are, independently, $C_{1-6}$ alkyl (optionally substituted by halogen) or phenyl (itself optionally substituted by halogen, hydroxy, nitro, $NH_2$, $NH(C_{1-4}$ alkyl), $N(C_{1-4}$ alkyl)$_2$, $S(O)_2(C_{1-4}$ alkyl), $S(O)_2NH_2$, $S(O)_2NH(C_{1-4}$ alkyl), $S(O)_2N(C_{1-4}$ alkyl)$_2$, cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$, $CO_2H$, $CO_2(C_{1-4}$ alkyl), $NHC(O)(C_{1-4}$ allyl), $NHS(O)_2(C_{1-4}$ alkyl), $C(O)(C_{1-4}$ alkyl), $CF_3$ or $OCF_3$).

When Z, $R^2$ and $R^a$ together with the carbon atom to which Z and $R^a$ are attached form a ring, the ring is, for example, a 2,3-dihydro-1H-inden-2-yl ring.

In yet another aspect $R^1$ is phenyl optionally substituted (for example independently mono- or di-substituted) with halogen (for example chlorine or fluorine), cyano, $C_{1-4}$ alkyl (for example methyl) or $C_{1-4}$ alkoxy (for example methoxy).

In a further aspect $R^1$ is phenyl optionally substituted (for example independently mono- or di-substituted) with halogen (for example chlorine or fluorine), $C_{1-4}$ alkyl (for example methyl) or $C_{1-4}$ alkoxy (for example methoxy).

In a still further aspect $R^1$ is phenyl optionally substituted (for example with one, two or three of the same or different) with fluorine, chlorine, cyano, $C_{1-4}$ alkyl (for example methyl) or $C_{1-4}$ alkoxy (for example methoxy).

In another aspect $R^1$ is phenyl optionally substituted (for example with one, two or three of the same or different) with fluorine, chlorine, $C_{1-4}$ alkyl (for example methyl) or $C_{1-4}$ alkoxy (for example methoxy).

In yet another aspect $R^1$ is phenyl substituted by one, two or three (for example two or three) substituents independently selected from: fluorine, chlorine, cyano and methyl.

In a further aspect $R^1$ is phenyl substituted by one, two or three (for example two or three) substituents independently selected from: fluorine, chlorine and methyl.

For example $R^1$ is 3,4dichlorophenyl, 2,4-dichloro-3-methylphenyl, 3,4-dichloro-2-methylphenyl, 2,4-dichlorophenyl, 4-chloro-2-methylphenyl or 4-fluorophenyl.

In a still further aspect of the invention $R^a$ is hydrogen.

In another aspect of the invention $R^b$ is hydrogen or methyl. In yet another aspect $R^b$ is hydrogen.

In a further aspect of the invention $R^c$ is hydrogen.

In a still further aspect of the invention $R^d$ is hydrogen, hydroxy or $C_{1-4}$ alkyl (such as methyl).

In another aspect Z is $CH_2$, $CH_2CH_2$, $CHCH_3$ or CHOH. In a further aspect Z is $CH_2$.

In another aspect $R^2$ is phenyl or heterocyclyl optionally substituted by halogen, cyano, nitro, hydroxy, $NR^7R^8$, $C_{1-6}$ alkyl (optionally substituted with halogen), $C_{1-6}$ alkoxy (optionally substituted with halogen), $S(O)_p(C_{1-6}$ alkyl), $S(O)_r CF_3$ or $S(O)_2NR^{14}R^{15}$; p and r are, independently, 0, 1 or 2; and $R^7$, $R^8$, $R^{14}$ and $R^{15}$ are, independently, hydrogen, $C_{1-6}$ alkyl (optionally substituted by halogen, hydroxy or $C_{3-10}$ cycloalkyl), $CH_2(C_{2-5}$ alkenyl), phenyl (itself optionally substituted by halogen, hydroxy, nitro, $NH_2$, $NH(C_{1-4}$ alkyl), $N(C_{1-4}$ alkyl)$_2$, $S(O)_2(C_{1-4}$ alkyl), $S(O)_2NH_2$, $S(O)_2NH(C_{1-4}$ alkyl), $S(O)_2N(C_{1-4}$ alkyl)$_2$ (and these alkyl groups may join to form a ring as described for $R^7$ and $R^8$ below) cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$ (and these alkyl groups may join to form a ring as described for $R^7$ and $R^8$ below), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$) or heterocyclyl (itself optionally substituted by halogen, hydroxy, nitro, $NH_2$, $NH(C_{1-4}$ alkyl), $N(C_{1-4}$ alkyl)$_2$, $S(O)_2(C_{1-4}$ alkyl), $S(O)_2NH_2$, $S(O)_2NH(C_{1-4}$ alkyl), $S(O)_2N(C_{1-4}$ alkyl)$_2$ (and these alkyl groups may join to form a ring as described for $R^7$ and $R^8$ below), cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$ (and these alkyl groups may join to form a ring as described for $R^7$ and $R^8$ below), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$); or alternatively $NR^7R^8$ or $NR^{14}R^{15}$ may, independently, form a 4-7 membered heterocyclic ring, azetidine, pyrrolidine, piperidine, azepine, morpholine or piperazine, the latter optionally substituted by $C_{1-4}$ alkyl on the distal nitrogen.

In yet another aspect of the invention $R^2$ is phenyl or heterocyclyl optionally substituted by halogen (such as fluoro or chloro), cyano, hydroxy, $C_{1-4}$ alkyl (such as methyl), $C_{1-4}$ haloalkyl (such as $CF_3$) or $C_{1-4}$ alkoxy (such as methoxy).

In a further aspect $R^2$ is phenyl or heterocyclyl optionally substituted by halogen (such as fluoro or chloro), $C_{1-4}$ alkyl (such as methyl), $C_{1-4}$ haloalkyl (such as $CF_3$) or $C_{1-4}$ alkoxy (such as methoxy).

In a still further aspect $R^2$ is phenyl optionally substituted by halogen (such as fluoro or chloro), cyano, hydroxy, or $C_{1-4}$ alkyl (such as methyl).

In another aspect heterocyclyl is indolyl, imidazolyl, thienyl or pyridinyl.

In yet another aspect the present invention provides a compound of formula (I) wherein: $R^c$ is hydrogen; X is O; Z is $CH_2$; $R^1$ is phenyl substituted by halogen (for example by one or two chlorine atoms) or $C_{1-4}$ alkyl (for example methyl); $R^2$ is phenyl or heterocyclyl optionally substituted by halogen (such as fluoro or chloro), $C_{1-4}$ alkyl (such as methyl), $C_{1-4}$ haloalkyl (such as $CF_3$) or $C_{1-4}$ alkoxy (such as methoxy); $R^b$ is hydrogen; and heterocyclyl is indolyl, imidazolyl, thienyl or pyridinyl. $R^a$ is hydrogen.

In a further aspect the present invention provides a compound of formula (I) wherein: $R^a$ and $R^c$ are both hydrogen; $R^b$ is hydrogen or $C_{1-4}$ alkyl (such as methyl or tert-butyl); X is O; Z is $CH_2$, $CH_2CH_2$, $CHCH_3$ or CHOH; $R^1$ is phenyl substituted by halogen (for example by one or two chlorine atoms), cyano or $C_{1-4}$ alkyl (for example methyl); $R^2$ is phenyl or heterocyclyl optionally substituted by halogen (such as fluoro or chloro), cyano, hydroxy, $C_{1-4}$ alkyl (such as methyl), $C_{1-4}$ haloalkyl (such as $CF_3$) or $C_{1-4}$ alkoxy (such as methoxy); and heterocyclyl is indolyl, imidazolyl, thienyl or pyridinyl; or a salt thereof (such as a dihydrochloride).

The compounds of the present invention can be prepared as described below.

A compound of formula (I) can be prepared by reacting a compound of formula (II):

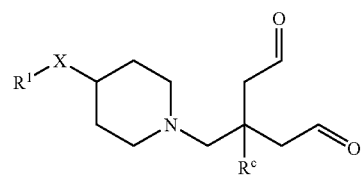

(II)

with a compound of formula (III):

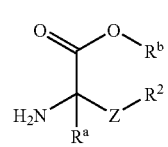

(III)

in the presence of $NaBH(OAc)_3$ or $NaBH_3(CN)$ in a suitable solvent (for example, an aliphatic alcohol such as methanol or ethanol) at a suitable temperature (such as in the range 0° C. to 30° C.).

Alternatively, a compound of formula (I), where $R^b$ is not hydrogen, can be prepared by reacting a compound of formula (II) with a compound of formula (III), where $R^b$ is not hydrogen, in the presence of $NaBH(OAc)_3$ in the presence of a suitable base (such as triethylamine) in a suitable solvent (such as tetrahydrofuran) at a suitable temperature (such as in the range 0° C. to 30° C.).

For a compound of formula (I):
when $R^b$ is hydrogen said compound may be converted to a compound of the invention where $R^b$ is not hydrogen by a standard esterification method well known in the art; and,
when $R^b$ is not hydrogen said compound may be converted to a compound of the invention where $R^b$ is hydrogen by a standard ester hydrolysis method well known in the art.

Such methods are described in undergraduate organic chemistry textbooks (such as Advanced Organic Chemistry by J March, 5$^{th}$ edition M B Smith and J March, Wiley, 2001).

A compound of formula (II) can be prepared by reacting a compound of formula (IV):

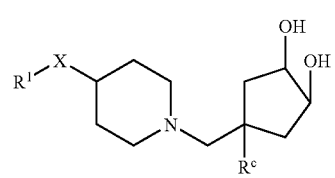

(IV)

with lead tetra-acetate in the presence of sodium carbonate in dichloromethane.

A compound of formula (IV) can be prepared by reducing a compound of formula (V):

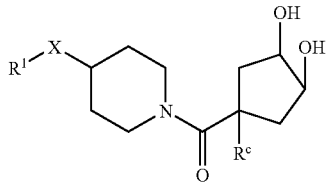
(V)

with borane in tetrahydrofuran at reflux.

A compound of formula (V) can be prepared by oxidising a compound of formula (VI):

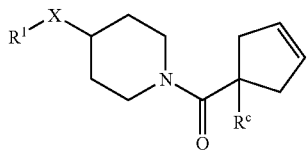
(VI)

with osmium tetroxide in the presence of N-methyl morpholine N-Oxide (NMMO) in aqueous acetone at ambient (for example 10-30° C.) temperature.

A compound of formula (VI) can be prepared by coupling a compound of formula (VII):

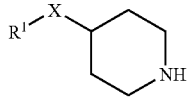
(VII)

and a compound of formula (VIII):

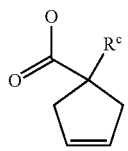
(VIII)

under conventional conditions (such as EDCI/HOBT/DMAP) in dichloromethane at ambient (for example 10-30° C.) temperature.

Alternatively a compound of formula (I) wherein $R^a$ represents H may be prepared by reaction of a compound of formula (IX) with a compound of formula (X) wherein L is a suitable leaving group (for example bromide, triflate or methanesulfonate) in a suitable solvent, for example dichloromethane, at a temperature in the range 0° C. to 30° C., in the presence of a base (such as a tri($C_{1-6}$ alkyl)amine, for example triethylamine or Hunig's base).

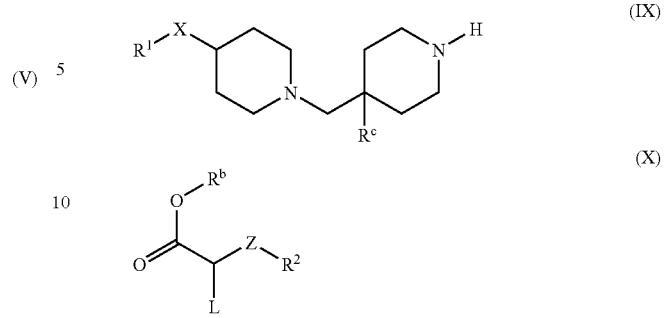
(IX)

(X)

A compound of formula (IX) can be prepared by deprotecting a compound of formula (XI):

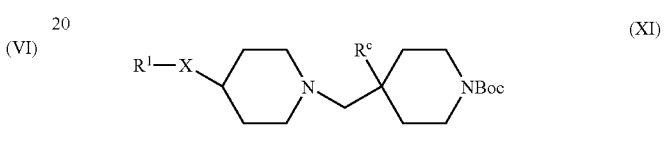
(XI)

for example using trifluoroacetic acid in a suitable solvent (such as dichloromethane) or using a source of hydrogen chloride in a suitable solvent (such as dioxane).

A compound of formula (XI), wherein $R^c$ is hydrogen, can be prepared by reacting a compound of formula (VII) with a compound of formula (XII):

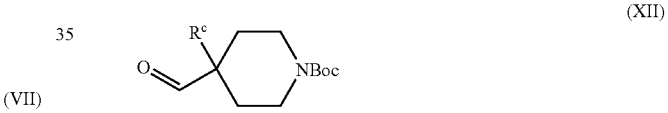
(XII)

in the presence of $NaBH(OAc)_3$ and acetic acid, in a suitable solvent (such as tetrahydrofuran or dichloromethane).

A compound of formula (XI), wherein $R^c$ is hydroxy, can be prepared by reacting a compound of formula (XI) with a compound of formula (XIII):

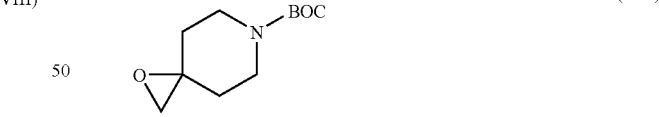
(XIII)

in a suitable solvent (such as a $C_{1-6}$ aliphatic alcohol, for example ethanol) at room temperature (0° C. to 30° C., such as 15° C. to 30° C.).

Alternatively a compound of formula (I) wherein $R^a$ represents H may be prepared by hydrolysis of a compound of formula (XIV), wherein Xc represents a chiral auxiliary of a type well-known in the art (for example (4R,5S)-1,5dimethyl-4-phenylimidazolidin-2-one, (4R)-4-(phenylmethyl)-2-oxazolidinone, (4S)-4-(phenylmethyl)-2-oxazolidinone or (3aR,6S,7aS)-hexahydro-8,8-dimethyl-3H-3a,6-methano-2,1-benzisothiazole 2,2-dioxide), for example with aqueous sodium hydroxide in a suitable solvent (such as an aliphatic alcohol, for example methanol), at a temperature between 10° C. and reflux of the solvent, typically at about 45° C.

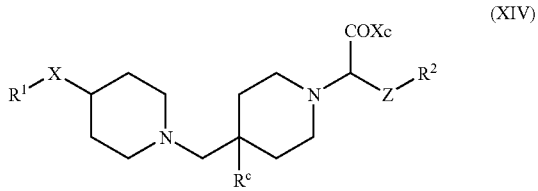

A compound of formula (XIV) may be prepared by deprotonation of a compound of formula (XV) for example with lithium hexamethyl disilazide, at a temperature between −78° C. and 0° C. followed by reaction with a compound of formula (XVI), at a temperature between −78° C. and 0° C., typically at −20° C.

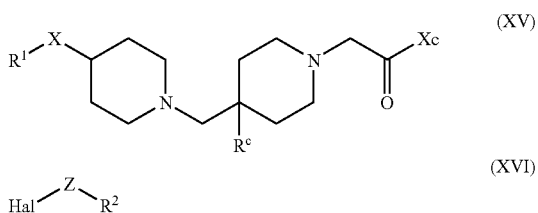

A compound of formula (XV) may be prepared by reaction of a compound of formula (IX) with a compound of formula (XVII) in a suitable solvent, for example tetrahydrofuran in the presence of a base, for example aqueous sodium bicarbonate, at ambient temperature.

Further compounds of formula (I) can be prepared by adaptation of: the routes described above, methods described in the art or the Examples recited below.

Compounds of formula (III), (VII), (VIII) and (XVII) can be prepared by using or adapting methods described in the art. The preparation of various phenoxy piperidines is described in WO 01/77101.

In the above processes it may be desirable or necessary to protect an acid group or a hydroxy or other potentially reactive group. Suitable protecting groups and details of processes for adding and removing such groups may be found in "Protective Groups in Organic Synthesis", 3rd Edition (1999) by Greene and Wuts.

In another aspect the present invention provides processes for the preparation of compounds of formula (I).

The compounds of formula (I) have activity as pharmaceuticals, in particular as modulators of chemokine receptor (for example CCR3) activity, and may be used in the treatment of autoimmune, inflammatory, proliferative or hyperproliferative diseases, or immunologically-mediated diseases (including rejection of transplanted organs or tissues and Acquired Immunodeficiency Syndrome (AIDS)).

Examples of these conditions are:

(1) (the respiratory tract) obstructive diseases of airways including: chronic obstructive pulmonary disease (COPD) (such as irreversible COPD); asthma {such as bronchial, allergic, intrinsic, extrinsic or dust asthma, particularly chronic or inveterate asthma (for example late asthma or airways hyper-responsiveness)}; bronchitis {such as eosinophilic bronchitis}; acute, allergic, atrophic rhinitis or chronic rhinitis including rhinitis caseosa, hypertrophic rhinitis, rhinitis purulenta, rhinitis sicca or rhinitis medicamentosa; membranous rhinitis including croupous, fibrinous or pseudomembranous rhinitis or scrofulous rhinitis; seasonal rhinitis including rhinitis nervosa (hay fever) or vasomotor rhinitis; sarcoidosis; farmer's lung and related diseases; nasal polyposis; fibroid lung, idiopathic interstitial pneumonia, antitussive activity, treatment of chronic cough associated with inflammatory conditions of the airways or iatrogenic induced cough;

(2) (bone and joints) arthrides including rheumatic, infectious, autoimmune, seronegative spondyloarthropathies (such as ankylosing spondylitis, psoriatic arthritis or Reiter's disease), Behcet's disease, Sjogren's syndrome or systemic sclerosis;

(3) (skin and eyes) psoriasis, atopic dermatitis, contact dermatitis or other eczmatous dermitides, seborrhoetic dermatitis, lichen planus, phemphigus, bullous phemphigus, epidermolysis bullosa, urticaria, angiodermas, vasculitides erythemas, cutaneous eosinophilias, uveitis, alopecia areata, corneal ulcer or vernal conjunctivitis;

(4) (gastrointestinal tract) Coeliac disease, proctitis, eosinophilic gastro-enteritis, mastocytosis, Crohn's disease, ulcerative colitis, irritable bowel disease or food-related allergies which have effects remote from the gut (for example migraine, rhinitis or eczema);

(5) (Allograft rejection) acute and chronic following, for example, transplantation of kidney, heart, liver, lung, bone marrow, skin or cornea; or chronic graft versus host disease; and/or (6) (other tissues or diseases) Alzheimer's disease, multiple sclerosis, atherosclerosis, Acquired Immunodeficiency Syndrome (AIDS), lupus disorders (such as lupus erythematosus or systemic lupus), erythematosus, Hashimoto's thyroiditis, myasthenia gravis, type I diabetes, nephrotic syndrome, eosinophilia fascitis, hyper IgE syndrome, leprosy (such as lepromatous leprosy), peridontal disease, Sezary syndrome, idiopathic thrombocytopenia pupura or disorders of the menstrual cycle.

The compounds of formula (I) or a pharmaceutically acceptable salt thereof or a solvate thereof, are also H1 antagonists (and can, therefore, be used in the treatment of allergic disorders); and may also be used to control a sign and/or symptom of what is commonly referred to as a cold (for example a sign and/or symptom of a common cold or influenza or other associated respiratory virus infection).

According to a further feature of the present invention there is provided a method for treating a chemokine mediated disease state (for example a CCR3 mediated disease state) in a mammal, such as man, suffering from, or at risk of, said disease state, which comprises administering to a mammal in need of such treatment a therapeutically effective amount of a compound of the formula (I) or a pharmaceutically acceptable salt thereof or a solvate thereof.

According to another feature of the present invention there is provided a method for antagonising H1 in a mammal, such as man, suffering from, or at risk of, an H1 mediated disease state, which comprises administering to a mammal in need of such treatment a therapeutically effective amount of a compound of the formula (I) or a pharmaceutically acceptable salt thereof or a solvate thereof.

According to yet another feature of the present invention there is provided a method for treating a sign and/or symptom of what is commonly referred to as a cold in a mammal, such as man, suffering from, or at risk of, said disease state, which comprises administering to a mammal in need of such treatment a therapeutically effective amount of a compound of the formula (I) or a pharmaceutically acceptable salt thereof or a solvate thereof.

The invention also provides a compound of the formula (I), or a pharmaceutically acceptable salt thereof or a solvate thereof, for use in therapy.

In another aspect the invention provides the use of a compound of formula (I), or a pharmaceutically acceptable salt thereof or a solvate thereof, in the manufacture of a medicament for use in therapy (for example modulating chemokine receptor activity (for example CCR3 receptor activity), antagonising H1 or treating a sign and/or symptom of what is commonly referred to as a cold).

The invention further provides the use of a compound of formula (I), or a pharmaceutically acceptable salt thereof, in the manufacture of a medicament for use in the treatment of:

(1) (the respiratory tract) obstructive diseases of airways including: chronic obstructive pulmonary disease (COPD) (such as irreversible COPD); asthma {such as bronchial, allergic, intrinsic, extrinsic or dust asthma, particularly chronic or inveterate asthma (for example late asthma or airways hyper-responsiveness)}; bronchitis {such as eosinophilic bronchitis}; acute, allergic, atrophic rhinitis or chronic rhinitis including rhinitis caseosa, hypertrophic rhinitis, rhinitis purulenta, rhinitis sicca or rhinitis medicamentosa; membranous rhinitis including croupous, fibrinous or pseudomembranous rhinitis or scrofulous rhinitis; seasonal rhinitis including rhinitis nervosa (hay fever) or vasomotor rhinitis; sarcoidosis; farmer's lung and related diseases; nasal polyposis; fibroid lung, idiopathic interstitial pneumonia, antitussive activity, treatment of chronic cough associated with inflammatory conditions of the airways or iatrogenic induced cough;

(2) (bone and joints) arthrides including rheumatic, infectious, autoimmune, seronegative spondyloarthropathies (such as ankylosing spondylitis, psoriatic arthritis or Reiter's disease), Behcet's disease, Sjogren's syndrome or systemic sclerosis;

(3) (skin and eyes) psoriasis, atopic dermatitis, contact dermatitis or other eczmatous dermitides, seborrhoetic dermatitis, lichen planus, phemphigus, bullous phemphigus, epidermolysis bullosa, urticaria, angiodermas, vasculitides erythemas, cutaneous eosinophilias, uveitis, alopecia areata, corneal ulcer or vernal conjunctivitis;

(4) (gastrointestinal tract) Coeliac disease, proctitis, eosinophilic gastro-enteritis, mastocytosis, Crohn's disease, ulcerative colitis, irritable bowel disease or food-related allergies which have effects remote from the gut (for example migraine, rhinitis or eczema);

(5) (Allograft rejection) acute and chronic following, for example, transplantation of kidney, heart, liver, lung, bone marrow, skin or cornea; or chronic graft versus host disease; and/or (6) (other tissues or diseases) Alzheimer's disease, multiple sclerosis, atherosclerosis, Acquired Immunodeficiency Syndrome (AIDS), lupus disorders (such as lupus erythematosus or systemic lupus), erythematosus, Hashimoto's thyroiditis, myasthenia gravis, type I diabetes, nephrotic syndrome, eosinophilia fascitis, hyper IgE syndrome, leprosy (such as lepromatous leprosy), Peridontal disease, sezary syndrome, idiopathic thrombocytopenia pupura or disorders of the menstrual cycle;

in a mammal (for example man).

In a further aspect the invention provides a compound of formula (I), or a pharmaceutically acceptable salt thereof, for use in the treatment of asthma {such as bronchial, allergic, intrinsic, extrinsic or dust asthma, particularly chronic or inveterate asthma (for example late asthma or airways hyper-responsiveness)}; or rhinitis {including acute, allergic, atrophic or chronic rhinitis, such as rhinitis caseosa, hypertrophic rhinitis, rhinitis purulenta, rhinitis sicca or rhinitis medicamentosa; membranous rhinitis including croupous, fibrinous or pseudomembranous rhinitis or scrofulous rhinitis; seasonal rhinitis including rhinitis nervosa (hay fever) or vasomotor rhinitis}.

In a still further aspect a compound of formula (I), or a pharmaceutically acceptable salt thereof, is useful in the treatment of asthma.

The present invention also provides a the use of a compound of formula (I), or a pharmaceutically acceptable salt thereof, in the manufacture of a medicament for use in the treatment of asthma {such as bronchial, allergic, intrinsic, extrinsic or dust asthma, particularly chronic or inveterate asthma (for example late asthma or airways hyper-responsiveness)}; or rhinitis {including acute, allergic, atrophic or chronic rhinitis, such as rhinitis caseosa, hypertrophic rhinitis, rhinitis purulenta, rhinitis sicca or rhinitis medicamentosa; membranous rhinitis including croupous, fibrinous or pseudomembranous rhinitis or scrofulous rhinitis; seasonal rhinitis including rhinitis nervosa (hay fever) or vasomotor rhinitis}.

In order to use a compound of the invention, or a pharmaceutically acceptable salt thereof or solvate thereof, for the therapeutic treatment of a mammal, such as man, said ingredient is normally formulated in accordance with standard pharmaceutical practice as a pharmaceutical composition. Therefore in another aspect the present invention provides a pharmaceutical composition which comprises a compound of the formula (I), or a pharmaceutically acceptable salt thereof or a solvate thereof (active ingredient), and a pharmaceutically acceptable adjuvant, diluent or carrier.

In a further aspect the present invention provides a process for the preparation of said composition which comprises mixing active ingredient with a pharmaceutically acceptable adjuvant, diluent or carrier. Depending on the mode of administration, the pharmaceutical composition will, for example, comprise from 0.05 to 99% w (percent by weight), such as from 0.05 to 80% w, for example from 0.10 to 70% w, such as from 0.10 to 50% w, of active ingredient, all percentages by weight being based on total composition.

The pharmaceutical compositions of this invention may be administered in standard manner for the disease condition that it is desired to treat, for example by topical (such as to the lung and/or airways or to the skin), oral, rectal or parenteral administration. For these purposes the compounds of this invention may be formulated by means known in the art. A suitable pharmaceutical composition of this invention is one suitable for oral administration in unit dosage form, for example a tablet or capsule which contains between 0.1 mg and 1 g of active ingredient.

Each patient may receive, for example, a dose of 0.01 mgkg$^{-1}$ to 100 mgkg$^{-1}$, for example in the range of 0.1 mgkg$^{-1}$ to 20 mgkg$^{-1}$, of the active ingredient administered, for example, 1 to 4 times per day.

The invention further relates to combination therapies wherein a compound of formula (1) or a pharmaceutically acceptable salt, solvate or in vivo hydrolysable ester thereof, or a pharmaceutical composition or formulation comprising a compound of formula (1) is administered concurrently or sequentially or as a combined preparation with another therapeutic agent or agents, for the treatment of one or more of the conditions listed.

In particular, for the treatment of the inflammatory diseases such as (but not restricted to) rheumatoid arthritis, osteoarthritis, asthma, allergic rhinitis, chronic obstructive pulmonary disease (COPD), psoriasis, and inflammatory bowel disease, the compounds of the invention may be combined with agents such as:—Non-steroidal anti-inflammatory agents (hereinafter NSAIDs) including non-selective cyclo-oxygenase (COX)-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate, leflunomide; hydroxychloroquine, d-penicillamine, auranofin or other parenteral or oral gold preparations; analgesics; diacerein; intra-articular therapies such as hyaluronic acid derivatives; and nutritional supplements such as glucosamine.

The present invention still further relates to the combination of a compound of the invention together with a cytokine or agonist or antagonist of cytokine function, (including agents which act on cytokine signalling pathways such as modulators of the SOCS system) including alpha-, beta-, and gamma-interferons; insulin-like growth factor type I (IGF-1); interleukins (IL) including IL1 to 17, and interleukin antagonists or inhibitors such as anakinra; tumour necrosis factor alpha (TNF-α) inhibitors such as anti-TNF monoclonal antibodies (for example infliximab; adalimumab, and CDP-870) and TNF receptor antagonists including immunoglobulin molecules (such as etanercept) and low-molecular-weight agents such as pentoxyfylline.

The present invention still further relates to the combination of a compound of the invention together with modulators of chemokine receptor function such as antagonists of CCR1, CCR2, CCR2A, CCR2B, CCR4, CCR5, CCR6, CCR7, CCR8, CCR9, CCR10 and CCR11 (for the C-C family); CXCR1, CXCR2, CXCR3, CXCR4 and CXCR5 (for the C-X-C family) and $CX_3CR1$ for the $C-X_3-C$ family.

The present invention still further relates to the combination of a compound of the invention together with an inhibitor of matrix metalloproteases (MMps), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12, including agents such as doxycycline.

The present invention still further relates to the combination of a compound of the invention together with a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; N-(5-substituted)-thiophene-2-alkylsulfonamides; 2,6-di-tert-butylphenolhydrazones; methoxytetrahydropyrans such as Zeneca ZD-2138; the compound SB-210661; pyridinyl-substituted 2-cyanonaphthalene compounds such as L-739,010; 2-cyanoquinoline compounds such as L-746,530; indole and quinoline compounds such as MK-591, MK-886, and BAYx1005.

The present invention still further relates to the combination of a compound of the invention together with a receptor antagonist for leukotrienes (LT) B4, LTC4, LTD4, and LTE4. selected from the group consisting of the phenothiazin-3-1s such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAYx7195.

The present invention still further relates to the combination of a compound of the invention together with a phosphodiesterase (PDE) inhibitor such as the methylxanthanines including theophylline and aminophylline; and selective PDE isoenzyme inhibitors including PDE4 inhibitors and inhibitors of the isoform PDE4D, and inhibitors of PDE5.

The present invention still further relates to the combination of a compound of the invention together with histamine type 1 receptor antagonists such as cetirizine, loratadine, desloratadine, fexofenadine, acrivastine, terfenadine, astemizole, azelastine, levocabastine, chlorpheniramine, promethazine, cyclizine, and mizolastine applied orally, topically or parenterally.

The present invention still further relates to the combination of a compound of the invention together with a proton pump inhibitor (such as omeprazole) or gastroprotective histamine type 2 receptor antagonist.

The present invention still further relates to the combination of a compound of the invention with antagonists of the histamine type 4 receptor.

The present invention still further relates to the combination of a compound of the invention together with an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride, and ethylnorepinephrine hydrochloride.

The present invention still further relates to the combination of a compound of the invention together with anticholinergic agents including muscarinic receptor (M1, M2, and M3) antagonists such as atropine, hyoscine, glycopyrrrolate, ipratropium bromide, tiotropiwn bromide, oxitropium bromide, pirenzepine, and telenzepine.

The present invention still further relates to the combination of a compound of the invention together with a beta-adrenoceptor agonist (including beta receptor subtypes 1-4) such as isoprenaline, salbutamol, formoterol, salmeterol, terbutaline, orciprenaline, bitolterol mesylate, and pirbuterol, including chiral enantiomers thereof.

The present invention still further relates to the combination of a compound of the invention together with a chromone, including sodium cromoglycate and nedocromil sodium.

The present invention still further relates to the combination of a compound of the invention together with a glucocorticoid, such as flunisolide, triamcinolone acetonide, beclomethasone dipropionate, budesonide, fluticasone propionate, ciclesonide, and mometasone furoate.

The present invention still further relates to the combination of a compound of the invention together with an agent that modulate nuclear hormone receptors such as PPARs.

The present invention still further relates to the combination of a compound of the invention together with an immunoglobulin (Ig) or Ig preparation or an antagonist or antibody modulating Ig function such as anti-IgE (e.g. omalizumab).

The present invention still further relates to the combination of a compound of the invention together with other systemic or topically-applied anti-inflammatory agents including thalidomide and derivatives, retinoids, dithranol, and calcipotriol.

The present invention still further relates to the combination of a compound of the invention together with combinations of aminosalicylates and sulfapyridine such as sulfasalazine, mesalazine, balsalazide, and olsalazine; and immunomodulatory agents such as the thiopurines, and corticosteroids such as budesonide.

The present invention still further relates to the combination of a compound of the invention together with an antibacterial agent including penicillin derivatives, tetracyclines, macrolides, beta-lactams, fluoroquinolones, metronidazole, and inhaled aminoglycosides; and antiviral agents including acyclovir, famciclovir, valaciclovir, ganciclovir, cidofovir; amantadine, rimantadine; ribavirin; zanamavir and oseltamavir, protease inhibitors such as indinavir, nelfinavir, ritonavir, and saquinavir; nucleoside reverse transcriptase inhibitors such as didanosine, lamivudine, stavudine, zalcitabine, zidovudine; non-nucleoside reverse transcriptase inhibitors such as nevirapine, efavirenz.

The present invention still further relates to the combination of a compound of the invention together with cardiovascular agents such as calcium channel blockers, beta-adrenoceptor blockers, angiotensin-converting enzyme (ACE) inhibitors, angiotensin-2 receptor antagonists; lipid lowering agents such as statins, and fibrates; modulators of blood cell morphology such as pentoxyfylline; thrombolytics, and anticoagulants including platelet aggregation inhibitors.

The present invention still further relates to the combination of a compound of the invention together with CNS agents such as antidepressants (such as sertraline), anti-Parkinsonian drugs (such as deprenyl, L-dopa, ropinirole, pramipexole, MAOB inhibitors such as selegine and rasagiline, comP inhibitors such as tasmar, A-2 inhibitors, dopamine reuptake inhibitors, NMDA antagonists, nicotine agonists, dopamine agonists and inhibitors of neuronal nitric oxide synthase), and anti-Alzheimer's drugs such as donepezil, rivastigmine, tacrine, COX-2 inhibitors, propentofylline or metrifonate.

The present invention still further relates to the combination of a compound of the invention together with agents for the treatment of acute and chronic pain, including centrally and peripherally-acting analgesics such as opioid analogues and derivatives, carbamazepine, phenytoin, sodium valproate, amitryptiline and other antidepressant agents, paracetamol, and non-steroidal anti-inflammatory agents.

The present invention still further relates to the combination of a compound of the invention together with parenterally or topically-applied (including inhaled) local anaesthetic agents such as lignocaine and analogues.

The compounds of the present invention may also be used in combination with anti-osteoporosis agents including hormonal agents such as raloxifene, and biphosphonates such as alendronate.

The present invention still further relates to the combination of a compound of the invention together with (i) tryptase inhibitors; (ii) platelet activating factor (PAF) antagonists; (iii) interleukin converting enzyme (ICE) inhibitors; (iv) IMPDH inhibitors; (v) adhesion molecule inhibitors including VLA4 antagonists; (vi) cathepsins; (vii) Kinase inhibitors including but not limited to inhibitors of tyrosine kinases (such as Btk, Itk, Jak3 MAP examples of inhibitors might include Gefitinib, Imatinib mesylate), Serine/threonine kinases (including but not limited to inhibitors of MAP kinases such as p38, JNK, protein kinases A, B and C and IKK), and kinases involved in cell cycle regulation (such as but not limited to the cylin dependent kinases); (viii) glucose-6 phosphate dehydrogenase inhibitors; (ix) kinin-$B_1$- and $B_2$-receptor antagonists; (x) anti-gout agents, e.g., colchicine; (xi) xanthine oxidase inhibitors, e.g., allopurinol; (xii) uricosuric agents, e.g., probenecid, sulfinpyrazone, and benzbromarone; (xiii) growth hormone secretagogues; (xiv) transforming growth factor (TGPFβ); (xv) platelet-derived growth factor (PDGF); (xvi) fibroblast growth factor, e.g., basic fibroblast growth factor (bPGF); (xvii) granulocyte macrophage colony stimulating factor (GM-CSF); (xviii) capsaicin cream; (xix) tachykinin $NK_1$ and $NK_3$ receptor antagonists such as the group consisting of NKP-608C; SB-233412. (talnetant); and D-4418; (xx) elastase inhibitors such as the group consisting of UT-77 and ZD-0892; (xxi) TNF-alpha converting enzyme inhibitors (TACE); (xxii) induced nitric oxide synthase (iNOS) inhibitors or (xxiii) chemoattractant receptor-homologous molecule expressed on TH2 cells, (such as CRTH2 antagonists) (xxiv) inhibitors of P38 (xxv) agents modulating the function of Toll-like receptors (TLR) and (xxvi) agents modulating the activity of purinergic receptors such as P2X7; (xxvii) inhibitors of transcription factors activation such as NFkB, API, and STATS.

The compounds of the invention can also be used in combination with existing therapeutic agents for the treatment of cancer. Suitable agents to be used in combination include:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside, hydroxyurea, gemcitabine and paclitaxel; antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecins);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) Agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido- N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab, compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPIT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapeutic approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell energy, approaches using transfected immune cells such as cytokine-transfected dendritic cells, approaches using cytokine-transfected tumour cell lines and approaches using anti-idiotypic antibodies.

The invention will now be-illustrated by the following non-limiting examples in which, unless stated otherwise:

(i) when given, $^1$H NMR data is quoted and is in the form of delta values for major diagnostic protons, given in parts per million (ppm) relative to tetramethylsilane EMS) as an internal standard, determined at 300 MHz or 400 MHz using perdeuterio DMSO-D6 ($CD_3SOCD_3$) or $CDCl_3$ as the solvent unless otherwise stated;

(ii) mass spectra (MS) were run with an electron energy of 70 electron volts in the chemical ionisation (CI) mode using a direct exposure probe; where indicated ionisation was effected by electron impact (EI) or fast atom bombardment (FAB); where values for m/z are given, generally only ions which indicate the parent mass are reported, and unless otherwise stated the mass ion quoted is the positive mass ion—(M+H)$^+$;

(iii) the title and sub-title compounds of the examples and methods were named using the index name program from Advanced Chemistry Development Inc, version 6.00;

(iv) unless stated otherwise, reverse phase HPLC was conducted using a "Symmetry", "NovaPak" or "Xerra" reverse phase silica column;

(v) for analytical HPLC the following conditions were used:
Reverse phase analytical HPLC (Hewlett Packard Series 1100) using Waters "Symmetry" C8 column 3.5 μm; 4.6× 50 mm column using 0.1% ammonium acetate/acetonitrile gradients at 2 mL/min given as % aqueous
STANDARD 75% to 5% over 3 min
FAST 45% to 5% over 2.5. min
MEDIUM FAST 65% to 5% in 2.5 min
SLOW 95% to 50% in 2.5 min
SUPERSLOW 100% to 80% in 2.5 min; and (vi) the following abbreviations are used.

| | |
|---|---|
| HOBT | 1-hydroxybenzotriazole |
| DMSO | dimethylsulfoxide |
| HPLC | high pressure liquid chromatography |
| EDCI | 1-ethyl-3-(3-dimethylaminopropyl)carbodi-imide hydrochloride |
| DMAP | N,N-dimethylaminopyridine |
| TFA | trifluoroacetic acid |
| min | minutes |
| h | hour |

Intermediate 1

4-[[4-(3,4-Dichlorophenoxy)-1-piperidinyl]methyl]-1,2-cyclopentanediol a) 1-(3-Cyclopenten-1-ylcarbonyl)-4-(3,4-dichlorophenoxy)-piperidine 3,4-Dichlorophenoxypiperidine (3.09 g) was dissolved in dichloromethane (80 mL). HOBT (1.77 g) and DMAP (0.44 g) were added followed by a solution of 3-cyclopentene-1-carboxylic acid (1.45 g) in dichloromethane (5 mL). EDCI (2.45 g) was added and the solution was stirred for 60 h. Water (100 mL) was added and the phases were separated. The aqueous phase was extracted with dichloromethane (2×40 mL). The organic phases were combined, dried ($MgSO_4$), filtered and evaporated to give subtitle compound (3.40 g) that was used without further purification.

MS [M+H]$^+$ (ES+) 340/342 $^1$H NMR δ $_{(CDCl3)}$ 4.47-4.53 (1H, m), 5.67 (2H, s), 7.33 (1H, d), 6.78 (1H, dd), 7.02 (1H, d), 3.62-3.84 (3H, m), 3.44-3.52 (1H, m), 3.33 (1H, d), 2.68-2.77 (2H, m), 2.54-2.64 (2H, m), 1.88-1.99 (2H, m), 1.73-1.86 (2H, m).

b) 4-[[4-(3,4-Dichlorophenoxy)-1-piperidinyl]carbonyl]-1,2-cyclopentanediol 1-(3Cyclopenten-1-ylcarbonyl)-4-(3,4-dicblorophenoxy)-piperidine (1.33 g) was dissolved in acetone (30 mL) and water (20 mL). N-methylmorpholine N-oxide (1.12 g) was added followed by a solution of osmium tetroxide (1 mL of 2.5% in 2-methylpropan-2-ol) and the mixture was stirred for 60 h. Aqueous sodium metabisulfite solution (40 mL, saturated) was added followed by dichloromethane (50 mL) and the phases were separated. The organic phase was washed with ammonium chloride solution, dried, filtered and concentrated. The residue was purified by chromatography eluting with dichloromethane:methanol (24:1 then 37:3) to give the subtitle compound as a mixture of isomers:

Less polar isomer (0.31 g):

MS [M+H]$^+$ (ES+) 374/376 $^1$H NMR δ $_{(CDCl3)}$ 1.79-1.98 (6H, m), 2.12-2.22 (2H, m), 3.23 (1H, tt), 3.49-3.56 (1H, m), 3.65-3.79 (3H, m), 3.93 (1H, d), 3.99-4.08 (3H, m), 4.53 (1H, tt), 6.77 (1H, dd), 7.02 (1H, d), 7.34 (1H, d).

More polar isomer (0.71 g):

MS [M+H]$^+$ (ES+) 374/376 $^1$H NMR δ$_{(CDCl3)}$ 1.73-1.86 ((2H, m), 1.86-2.00 (4H, m), 2.07-2.16 (2H, m), 2.50-2.60 (2H, m), 3.39 (1H, tt), 3.42-3.48 (1H, m), 3.61-3.78 (3H, m), 4.22-4.27 (2H, m), 4.47-4.53 (1H, m), 6.77 (1H, dd) 7.01 (1H, d), 7.33 (1H, d).

c) 4-[[4-(3,4-Dichlorophenoxy)-1-piperidinyl]methyl]-1,2-cyclopentanediol

The more polar isomer of 4-[[4-(3,4dichlorophenoxy)-1-piperidinyl]carbonyl]-1,2-cyclopentanediol (0.71 g) was dissolved in a solution of borane in tetrahydrofuran (16 mL of 1M solution) and the mixture was heated to reflux for 1.5 h. Methanol (10 mL) was added and the solution was heated under reflux for 1 h. The volatile components were evaporated and the residue was loaded onto an HPLC SCX cartridge in methanol and eluted with methanol, then with 0.7M ammonia in methanol to give the title compound (0.73 g) as an oil.

MS [M+H]$^+$ (ES+) 360/362 (standard gradient, retention time 1.33)

Similar treatment of the minor isomer of 4-[[4-(3,4-dichlorophenoxy)-1-piperidinyl]carbonyl]-1,2-cyclopentanediol (0.30 g) gave the title compound (0.26 g) as an oil.

MS [M+H]$^+$ (ES+) 360/362 (standard gradient, retention time 1.33)

The following compounds were prepared by analogous routes starting from the appropriate phenoxypiperidine:

| Intermediate | Name | MS [M+H]$^+$ (ES+) |
|---|---|---|
| 2 | 4-[[4-(2,4-Dichloro-3-methylphenoxy)-1-piperidinyl]methyl]-1,2-cyclopentanediol | 374/376 |
| 3 | 4-[[4-(3,4-Dichloro-2-methylphenoxy)-1-piperidinyl]methyl]-1,2-cyclopentanediol | 374/376 |

Intermediate 4

4-(3,4Dichlorophenoxy)-1-(4-piperidinylmethyl)-piperidine a) 1,1-Dimethylethyl 4-[[4-(3,4-dichlorophenoxy)-1-piperidinyl]methyl]-1-piperidinecarboxylate 4-(3,4-Dichlorophenoxy)piperidine (1.27 g) was dissolved in tetrahydrofuran (20 mL); acetic acid (0.5 mL) and 1,1-dimethylethyl 4-formyl-1-piperidinecarboxylate (1.43 g) were added to the solution. The reaction mixture was stirred at room temperature for 30 min then sodium triacetoxyborohydride (1.53 g) was added and the mixture was stirred at room temperature overnight. The reaction mixture was poured into 2M sodium hydroxide solution (50 mL) and product was extracted with ether. The ether was washed with brine, dried, filtered and evaporated. Crude material was purified by flash chromatography (eluting with 979:20:1 dichloromethane:methanol:aqueous ammonia) to give the subtitle compound (2.15 g).

MS 443/445 [M+H]$^+$ (ES+) $^1$H NMR δ$_{(CDCl3)}$ 1.06 (2H, ddd), 1.45 (9H, s), 1.61-1.82 (5H, m), 1.92-1.98 (2H, m), 2.16-2.27 (4H, m), 2.65-2.73 (4H, m), 4.08 (2H, d), 4.25 (1H, dq), 6.75 (1H, dd), 6.99 (1H, d), 7.30 (1H, d)

b) 4-(3,4-Dichlorophenoxy)-1-(4-piperidinylmethyl)-piperidine 1,1-Dimethylethyl 4-[[4-(3,4-dichlorophenoxy)-1-piperidinyl]methyl]-1-piperidinecarboxylate (1.0 g) was added to a mixture of 20% TFA in dichloromethane (20 mL) and the mixture was stirred at room temperature for 1 h. Solvent was removed by evaporation and 2M sodium hydroxide solution (25 mL) was added to the residue. Product was extracted with ethyl acetate. The organic phase was washed with brine, dried, filtered and evaporated to give the title compound (0.5 g).

MS 343/345 [M+H]$^+$ (ES+) $^1$H NMR δ$_{(CDCl3)}$ 1.10 (2H, qd), 1.60 (1H, qquintet), 1.73-1.83 (4H, m), 1.90-2.01 (2H, m), 2.16-2.26 (4H, m), 2.55-2.70 (4H, m), 3.09 (2H, d), 4.24 (1H, dquintet), 6.75 (1H, dd), 6.99 (1H, d), 7.27 (1H, d)

The following intermediates were prepared analogously from the appropriate aryloxy piperidine or arylmethylpiperidine:

| Intermediate | Name | M+H Retention time (conditions) | $^1$H NMR |
|---|---|---|---|
| 5 | 4-[(4-Fluorophenyl)methyl]-1-(4-piperidinylmethyl)-piperidine | 291 1.75 (standard) | δ$_{(CD3OD+DMSO)}$ 1.19-1.32(4H, m), 1.46-1.54(1H, m), 1.55-1.62(2H, m), 1.77-1.84(1H, m), 1.85-1.93(4H, m), 2.17(2H, d), 2.51(2H, d), 2.80-2.89(4H, m), 3.23-3.26(2H, m), 7.01(2H, t), 7.16(2H, dd) |
| 6 | 4-(4-Chloro-2-methylphenoxy)-1-(4-piperidinylmethyl)-piperidine | 323/325 | δ$_{(CDCl3)}$ 1.08-1.21(2H, m), 1.56-1.68(1H, m), 1.73-1.86(4H, m), 1.90-1.99(2H, m), 2.16-2.31(7H, m), 2.57-2.69(4H, m), 3.12(2H, d), 4.23-4.31(1H, m), 6.74(1H, d), 7.06(1H, dd), 7.11(1H, d) |

| Intermediate | Name | M+H Retention time (conditions) | ¹H NMR |
|---|---|---|---|
| 7 | 3-Chloro-4-[[1-(4-piperidinylmethyl)-4-piperidinyl]oxy]-benzonitrile | 334/336 | δ$_{(CD3OD)}$ 1.66-1.94(5H, m), 2.00-2.11(2H, m), 2.26(2H, d), 2.37-2.47(2H, m), 2.58-2.77(4H, m), 3.09(2H, d), 3.30(2H, s), 4.64-4.73(1H, m), 7.27(1H, d), 7.63-7.66(1H, m), 7.80(1H, d) |
| 8 | 2-Chloro-4-[[1-(4-piperidinylmethyl)-4-piperidinyl]oxy]-benzonitrile | 334/336 | δ$_{(CD3OD)}$ 1.21-1.32(2H, m), 1.74-1.90(5H, m), 1.99-2.10(2H, m), 2.26(2H, d), 2.31-2.40(2H, m), 2.67-2.79(4H, m), 3.11-3.21(2H, m), 4.52-4.62(1H, m), 7.05(1H, dd), 7.21(1H, d), 7.70(1H, d) |

Intermediate 9

(4S,5R)-1-[[4-[[4-(3,4-Dichlorophenoxy)-1-piperidinyl]methyl]-1-piperidinyl]acetyl]-3,4-dimethyl-5-phenyl-2-imidazolidinone 2,6Lutidine (18.26 mL) was added to a stirred suspension of (4R,5S)-1,5-dimethyl-4-phenylimidazolidin-2-one (27.33 g) in anhydrous tetrahydrofuran (300 mL) at 0° C. under nitrogen. Bromoacetyl bromide (11.95 mL) was added over 5 minutes and the mixture was stirred for a further 15 minutes. Saturated aqueous sodium bicarbonate solution (300 mL) was added followed by 4-(3,4-dichlorophenoxy)-1-(4-piperidinylmethyl)piperidine (44.86 g) and the mixture was stirred for 24 hours at ambient temperature. Water (300 mL) was added and the mixture was extracted with tert-butyl methyl ether (300 mL). The organic extracts were dried over anhydrous magnesium sulfate, filtered and evaporated under reduced pressure. The residue was suspended in tert-butyl methyl ether (300 mL) and stirred for 3 days. The resulting solid was filtered, washed with tert-butyl methyl ether (3×50 mL) and dried in under reduced pressure to give the title compound (45.65 g) as a solid.

MS (APCI) 573/575 [M+H]$^+$ ¹HNMR δ $_{(DMSO)}$ 0.67 (3H, d), 1.02 (2H, qd), 1.37-1.45 (1H, m), 1.55-1.62 (4H, m), 1.85-2.63 (2H, m), 2.02 (1H, t), 2.10 (2H, d), 2.10-2.19 (3H, m), 2.58-2.63 (2H, m), 2.70 (3H, s), 2.78 (2H, d), 3.60 (1H, d), 3.78 (1H, d), 3.96 (1H, dt), 4.39-4.46 (1H, m), 5.28 (1H, d), 6.97 (1H, dd), 7.12 (2H, d), 7.23 (1H, d), 7.27 (1H, t), 7.35 (2H, t), 7.48 (1H, d), (contains 1 equivalent of (4R,5S)-1,5-dimethyl-4-phenylimidazolidin-2-one).

EXAMPLE 1

(αS)-Methyl 4-[[4-(2,4dichloro-3-methylphenoxy)-1-piperidinyl]methyl]-α-(phenylmethyl)-1-piperidineacetate 4-[[4-(2,4-Dichloro-3-methylphenoxy)-1-piperidinyl]methyl]-1,2cyclopentanediol (0.30 g) was dissolved in dichloromethane (7 mL) and sodium carbonate (0.282 g) was added. The suspension was cooled to 0° C. Lead tetraacetate (0.389 g) was added over 20 minutes. The mixture was stirred for 40 min at 0° C.

The suspension was filtered through a plug of cotton wool into a solution of L-phenylalanine, methyl ester, hydrochloride salt (0.173 g), triethylamine (0.13 mL), acetic acid (0.06 mL), sodium triacetoxyborohydride (0.376 g) and tetrahydrofuran (12 mL). The reaction mixture was then stirred for 16 h at room temperature, poured into saturated aqueous sodium bicarbonate solution (50 mL), extracted into ethyl acetate (3×5 mL), washed with brine (50 mL), dried (MgSO$_4$), filtered, and concentrated. The residue was purified by column chromatography eluting with ethyl acetate, and further purified by HPLC (gradient ammonium acetate/acetonitrile 40:60 to 5:95) to give the title compound (0.205 g).

MS [M+H]$^+$ (ES+) 519/521

Examples 2-31 in TABLE I (below) were prepared by the method of Example 1 using the appropriate diol and aminoacid ester precursors.

EXAMPLE 32

(αS) Methyl 4-[[4-[(4-fluorophenyl)methyl]-1-piperidinyl]methyl]-α-(phenylmethyl)-1-piperidineacetate To a stirred, ice-cooled solution of methyl-(R)-3-phenyl lactate (0.191 g) and powdered 4 Å molecular sieves (0.27 g) in dichloromethane (2 mL) was added trifluoromethanesulfonic anhydride (0.195 mL). After 10 rain, 2,6-lutidine (0.27 mL) was added dropwise resulting in a deep red colour. The reaction mixture was stirred for 40 min at 0° C. A mixture of 4-[[4-[(4-fluorophenyl)methyl]-1-piperidinyl]methylpiperidine (0.28 g) and 4 Å molecular sieves (0.1 g) in dichloromethane (1.5 mL) was added. After 2 min, triethylamine (0.323 mL) was added and the reaction was allowed to warm to room temperature overnight. The reaction mixture was diluted with ethyl acetate and filtered. The filtrate was concentrated in vacuo and purified by flash column chromatography, eluting with ethyl acetate to yield a yellow solid (0.53 g).

Retention time: 2.37 min (Standard).

MS 453 [M+H]$^+$ (ES+). ¹H NMR δ$_{(CD3OD)}$ 1.43-1.58 (2H, m), 1.70-1.89 (6H, m), 2.31 (1H, td), 2.42 (1H, td), 2.61 (2H, d), 2.80-3.03 (9H, m), 3.03-3.10 (1H, m), 3.43-3.50 (3H, m), 3.55.(3H, s), 7.01 (2H, ddd), 7.14-7.28 (7H, m).

Examples 33-35 in TABLE I (below) were prepared by the method of Example 32 using the appropriate amines.

EXAMPLE 36

(αS) Methyl 4-[[4-(3,4-dichlorophenoxy)-1-piperidinyl]methyl]-α-[(2-hydroxyphenyl)methyl]-1-piperidineacetate (αS) Methyl 4-[[4-(3,4-dichlorophenoxy)-1-piperidinyl]methyl]-α-[(2-methoxyphenyl)methyl]-1-piperidineacetate (120 mg) in dichloromethane (6 mL) was cooled to −78 C under nitrogen, and a 1M solution of boron tribromide in dichloromethane (9 mL) was added dropwise to it. The mixture was then stirred at −78° C. for 30 minutes, and then at −5° C. for 30 minutes. The reaction mixture was then quenched carefully with methanol (20 mL), allowed to warm to room temperature and the volatiles removed in. vacuo. The residue was purified by reverse-phase HPLC using 75:25 to 5:95 0.1% aqueous ammonium acetate/acetonitrile over 6 minutes, symmetry column. This gave 67 mg of the title compound as an oil.

Lc/ms: RT 1.77 (fast). m/z 521/523 (M+H).

EXAMPLE 37

(αS)4-[[4-(2,4Dichloro-3-methylphenoxy)-1-piperidinyl]methyl]-α-(phenylmethyl)-1-piperidineacetic acid Methyl 4-[[4-(2,4-dichloro-3-methylphenoxy)-1-piperidinyl]methyl]-α-(phenylmethyl)-($α^1$S)-1-piperidineacetate (Example 1, 0.205 g), 6M hydrochloric acid (20 mL), and 2-propanol (5 mL) were heated together at 80° C. for 24 h, then cooled and concentrated under reduced pressure. The residue was purified by HPLC (gradient ammonium acetate/acetonitrile 75:25 to 5:95) to give the title compound (0.113 g).

MS [M+H]$^+$ (APCI+) 505/507. $^1$H NMR δ $_{(CD3OD)}$ 1.33-1.45 (2H, m), 1.71-1.82 (3H, m), 1.84-1.97 (4H, m), 2.28 (2H, d), 2.35 (3H, s), 2.37-2.47 (2H, m), 2.66-2.76 (2H, m), 2.87 (2H, q), 3.07-3.19 (2H, m), 3.40 (1H, d), 3.50 (1H, d), 3.63 (1H, t), 4.35-4.44 (1H, m), 6.86 (1H, d), 7.09-7.27 (6H, m).

Examples 38-70 in TABLE II (below) were prepared using the method of Example 37 from the appropriate ester (see TABLE I except for Example 58 which was prepared from (±) methyl 4-[[4-(3,4-dichlorophenoxy)-1-piperidinyl]methyl]-α-[(R)-[[(1,1-dimethylethyl)dimethylsilyl]oxy]phenylmethyl]-($α^1$S)-1-piperidineacetate [$^1$H NMR δ$_{(CDCl3)}$ 0.24 (6H, s), 1.07 (9H, s), 1.35-1.47 (2H, m), 1.67-1.74 (1H, m), 1.88-2.06 (4H, m), 2.15-2.24 (2H, m), 2.38-2.49 (4H, m), 2.60 (1H, t), 2.70 (1H, t), 2.86-2.94 (2H, m), 3.12 (1H, d), 3.36 (1H, d), 3.64 (3H, s), 4.36 (1H, q), 4.44-4.51 (1H, m), 5.19 (1H, d), 6.99 (1H, dd), 7.23 (1H, d), 7.43-7.57 (6H, m)] prepared analogously to Example 1 from the appropriate protected hydroxyaminoacid).

EXAMPLE 71

(αS)-4-[[4-(2,4-Dichloro-3-methylphenoxy-1-piperidinyl]methyl]-α-(phenylmethyl)-1-piperidineacetic acid, dihydrochloride salt (αS)-4-[[4-(2,4-Dichloro-3-methylphenoxy)-1-piperidinyl]methyl]-α-(phenylmethyl)-1-piperidineacetic acid Example 12, 0.062 g) was suspended in acetonitrile (5 mL) and a solution of hydrogen chloride in 1,4-dioxane (4M, 5 mL) was added. The suspension was concentrated under reduced pressure, and the process repeated again, to give the title compound (0.048 g).

MS [M+H]$^+$ (APCI+) 505/507 $^1$H NMR δ$_{(DMSO)}$ 1.43-1.65 (2H, m), 1.98-2.11 (4H, m), 2.18-2.30 (3H, m), 2.41 (3H, s), 2.44-2.56 (4H, m), 2.99-3.13 (6H, m), 3.43-3.51 (1H, m), 3.56-3.61 (1H, m), 3.64-3.74 (1H, m), 4.83-4.91 (1H, m), 7.19 (1H, t), 7.27 (3H, d), 7.30-7.36 (2H, m), 7.42 (1H, d).

Examples 72-78 in Table II were prepared from the appropriate ester (see Example 1 or TABLE I) following the method of Example 37 and either the salt crystallised from the hydrolysis step and was isolated by filtration or the product after chromatography was converted to the salt following the method of Example 71.

EXAMPLE 79

($α^1$S)-4-[[4-(3,4-Dichlorophenoxy-1-piperidinyl]methyl]-α-[(2-hydroxyphenyl)methyl]-1-piperidineacetic acid (αS) Methyl 4-[[4-(3,4dichlorophenoxy)-1-piperidinyl]methyl]-α-[(2 hydroxyphenyl)methyl]-1-piperidineacetate (Example 36, 67 mg) in methanol (4 mL) was stirred at room temperature under nitrogen. A solution of lithiun hydroxide (22 mg) in water (1 mL) was added dropwise to this, keeping the temperature below 30° C. The mixture was then stirred at room temperature for 20 hours. The volatiles were removed in vacuo and the residue was purified by HPLC using a gradient of 95:5 to 5:95 0.1% aqueous ammonium acetate/acetonitrile to give the title compound as a solid (48 mg).

MS: 505/507 (M+H) $^1$H NMR δ$_{(CD3OD)}$ 1.19-1.37 (2H, m), 1.52-1.62 (1H, m), 1.70-1.83 (4H, m), 1.94-2.03 (2H, m), 2.23 (2H, d), 2.30 (2H, t), 2.42 (1H, t), 2.66-2.74 (2H, m), 2.86 (1H, dd), 2.98-3.09 (2H, m), 3.15 (2H, d), 3.22 (1H, t), 4.32-4.42 (1H, m), 6.42 (1H, t), 6.61 (1H, dd), 6.82-6.89 (2H, m), 7.04 (1H, dd), 7.07 (1H, d), 7.36 (1H, d).

EXAMPLE 80

(αS)-4-[[4-(3,4Dichlorophenoxy)-1-piperidinyl]methyl]-α-(2-thienylmethyl)-1-piperidineacetic acid 4-[[4-(3,4-Dichlorophenoxy)-1-piperidinyl]methyl]-1,2-cyclopentanediol (0.20 g) was dissolved in dichloromethane (10 mL) and sodium carbonate (0.212 g) was added. The suspension was cooled to 0° C. Lead tetraacetate (0.248 g) was added over 20 minutes. The mixture was stirred for 40 min at 0° C.

MS [M+H]$^+$ (ES+) 358/360.

The suspension was filtered through a plug of cotton wool into a solution of α-amino-($α^2$S)-2-thiophenepropanoic acid (0.94 g) and acetic acid (0.1 mL) in ethanol (10 mL). Sodium triacetoxyborohydride (0.198 g) was added and the reaction mixture was stirred for 16 h at room temperature. The solvent was evaporated and the residue was redissolved in acetonitrile and filtered. This was purified by HPLC (gradient ammonium acetate/acetonitrile 95% to 50%) to give the title compound (0.048 g)

MS [M+H]$^+$ (ES+) 495/497. $^1$H NMR δ$_{(CD3OD)}$ 1.18-1.34 (3H, m), 1.52-1.61 (1H, m), 1.71-1.81 (4H, m), 1.95-2.03 (2H, m), 2.21-2.25 (2H, m), 2.26-2.52 (4H, m), 2.66-2.74 (2H, m), 2.91-3.15 (4H, m), 4.34-4.41 (1H, m), 6.83-6.90 (3H, m), 7.08 (1H, d), 7.12 (1H, dd), 7.37 (1H, d).

Example 81 in TABLE II was prepared following the method of Example 80 using the appropriate amino acid.

EXAMPLE 82

2-[4-[[4-(3,4-Dichlorophenoxy)-1-piperidinyl]methyl]-1-piperidinyl]-2,3-dihydro-1H-indene-2-carboxylic acid 4-[[4-(3,4-Dichlorophenoxy)-1-piperidinyl]methyl]-1,2-cyclopentanediol (0.20 g) was dissolved in dichloromethane (10 mL) and sodium carbonate (0.212 g) was added. The suspension was cooled to 0° C. Lead tetraacetate (0.248 g) was added over 20 minutes. The mixture was stirred for 40 min at 0° C.

MS [M+H]$^+$ (ES+) 358/360.

The suspension was filtered through a plug of cotton wool into a solution of 2-amino-2,3-dihydro-1H-indene-2-carboxylic acid hydrochloride (0.117 g), hydrochloric acid (0.1 mL), triethylamine (0.1 mL) and methanol (10 mL). Sodium cyanoborohydride (0.052 g) was added and the reaction mixture was stirred for 16 h at room temperature. The reaction mixture was diluted with saturated sodium bicarbonate solution. The aqueous phase was extracted with dichloromethane. The organic phases were dried (MgSO$_4$), filtered and evaporated and the residue was redissolved in acetonitrile. This was purified by HPLC (gradient ammonium acetate/acetonitrile 95% to 50%). The title compound crystallised from the HPLC fractions and was collected to give pure product (7 mg).

MS [M+H]$^+$ (ES+) 503/505. $^1$H NMR $\delta_{(CD3OD)}$ 1.21-1.36 (5H, m), 1.55-1.62 (1H, m), 1.72-1.81 (2H, m), 1.94-2.05 (2H, m), 2.16-2.25 (2H, m), 2.25-2.40 (3H, m), 2.66-2.74 (2H, m), 2.90-3.03 (4H, m), 3.66 (1H, s), 3.70 (1H, s), 4.34-4.41 (1H, m), 6.88 (1H, dd), 7.01-7.12 (5H, m), 7.37 (1H, d).

EXAMPLE 83

(αS)-4-[[4-(3,4-Dichlorophenoxy)-1-piperidinyl]methyl]-α-[(2-methylphenyl)methyl]-1-piperidineacetic acid A solution of lithium hexamethyldisilazide in tetrahydrofuran (1M, 131 mL) was added dropwise over 30 min to a stirred suspension (4S,5R)-1-[[4-[[4-(3,4-dichlorophenoxy)-1-piperidinyl]methyl]-1-piperidintyl]acetyl]-3,4-dimethyl-5-phpnyl-2-imidazolidinone (45.65 g) and 2-methylbenzyl bromide (16.3 mL) in anhydrous tetrahydrofuran (130 mL) at −°20° C. under nitrogen. After a further 20 hours at −20° C., water (300 mL) was added, the mixture was warmed to room temperature and then extracted with tert-butyl methyl ether (300 mL). The organic extracts were dried over anhydrous magnesium sulfate, filtered and evaporated under reduced pressure. The residue was dissolved in tetrahydrofuran (800 mL), then methanol (103 mL) and a solution of lithium hydroxide monohydrate (3.01 g) in water (194 mL) was added. The mixture was stirred at 50° C. for 16 hours then further lithium hydroxide monohydrate (3.01 g) was added. After a further 4 hours at 50° C., the mixture was cooled to room temperature. Water (600 mL), tert-butyl methyl ether (800 mL) and ammonium acetate (200 g) were added. The mixture was stirred rapidly for 3 days then the precipitate was collected by filtration of the two-phase mixture. The solid was washed with water (50 mL) then tert-butyl methyl ether (50 mL) and dried in vacuo at 50° C. to give the tide compound (8.90 g)

MS (APCI) 503/505 [M−H]$^{-1}$H NMR $\delta_{(CD3OD+NaOD)}$ 1.18-1.35 (2H, m), 1.52-1.62 (1H, m), 1.72-1.82 (4H, m), 2.23 (2H, d), 1.95-2.05 (2H, m), 2.26-2.42 (7H, m), 2.63-2.75 (2 m), 2.91 (1H, dd), 3.00 (1H, d), 3.05-3.10 (2H, m), 3.15 (1H, dd), 4.37-4.42 (1H, m), 6.88. (1H, dd), 6.98-7.10 (4H, m), 7.21-7.23 (1H, m), 7.37 (1H, d).

TABLE I

| Example | Name (NMR) | MS [M+H]$^+$ (ES+) |
|---|---|---|
| 2 | (αS) Methyl 4-[[4-(3,4-dichlorophenoxy)-1-piperidinyl]methyl]-α-(phenylmethyl)-1-piperidineacetate | 505/507 |
| 3 | (αR) Methyl 4-[[4-(3,4-dichlorophenoxy)-1-piperidinyl]methyl]-α-(phenylmethyl)-1-piperidineacetate | 505/507 |
| 4 | (αS) Methyl 4-[[4-(3,4-dichloro-2-methylphenoxy)-1-piperdinyl]methyl]-α-(phenylmethyl)-1-piperidineacetate | 519/521 |
| 5 | (αS) Methyl α-[(4-chlorophenyl)methyl]-4-[[4-(3,4-dichlorophenoxy)-1-piperidinyl]methyl]-1-piperidineacetate | 539/541/543 |
| 6 | (αS) Methyl 4-[[4-(3,4-dichlorophenoxy)-1-piperidinyl]methyl]-α-[(2-methylphenyl)methyl]-1-piperidineacetate | 519/521 |
| 7 | (αS) Methyl α-[4-[[4-(3,4-dichlorophenoxy)-1-piperidinyl]methyl]-1-piperidinyl]-3-pyridinepropanoate | 506/508 |
| 8 | (αS) Methyl 4-[[4-(3,4-dichlorophenoxy)-1-piperidinyl]methyl]-α-[(2-fluorophenyl)methyl]-1-piperidineacetate | 523/525 |
| 9 | (αS) Methyl 4-[[4-(3,4-dichlorophenoxy)-1-piperidinyl]methyl]-α-[[3-(trifluoromethyl)phenyl]methyl]-1-piperidineacetate | 573/575 |
| 10 | (αS) Methyl 4-[[4-(3,4-dichlorophenoxy)-1-piperidinyl]methyl]-α-[(4-methoxyphenyl)methyl]-1-piperidineacetate | 535/537 |
| 11 | (αS) Methyl α-[4-[[4-(3,4-dichlorophenoxy)-1-piperidinyl]methyl]-1-piperidinyl]-1H-indole-3-propanoate | 544/546 |
| 12 | (αS) 1,1-Dimethylethyl 4-[[4-(3,4-dichloro-2-methylphenoxy)-1-piperidinyl]methyl]-α-[(2-methylphenyl)methyl]-1-piperidineacetate | 575/577 |
| 13 | (αR) Methyl 4-[[4-(3,4-Dichloro-2-methylphenoxy)-1-piperidinyl]methyl]-α-(phenylmethyl)-1-piperidineacetate<br>$^1$H NMR $\delta_{(CD3OD)}$ 1.24(2H, td), 1.51-1.65(1H, m), 1.75-1.89(4H, m), 1.97-2.08(2H, m), 2.23-2.31(3H, m), 2.32-2.43(6H, m), 2.66-2.76(2H, m), 2.94-3.09(4H, m), 3.42-3.48(1H, m), 3.57(3H, s), 4.41-4.49(1H, m), 6.93(1H, d), 7.16-7.32(6H, m) | 519/521 |
| 14 | (αR) Methyl 4-[[4-(3,4-dichlorophenoxy)-1-piperidinyl]methyl]-α-[(2-methylphenyl)methyl]-1-piperidineacetate<br>$^1$H NMR $\delta_{(CD3OD)}$ 1.16-1.31(2H, m), 1.50-1.62(1H, m), 1.71-1.83(4H, m), 1.95-2.03(2H, m), 2.23(2H, d), 2.27-2.38(7H, m), 2.67-2.75(2H, m), 2.96-3.07(4H, m), 3.41(1H, dd), 3.51(3H, s), 4.35-4.42(1H, m), 6.88(1H, dd), 7.04-7.13(5H, m), 7.37(1H, d) | 519/521 |

TABLE I-continued

| Example | Name (NMR) | MS [M+H]+ (ES+) |
|---|---|---|
| 15 | (αS) Methyl 4-[[4-(3,4-dichlorophenoxy)-1-piperidinyl]methyl]-α-[(3-fluorophenyl)methyl]-1-piperidineacetate | 523/525 |
| 16 | (αS) Methyl 4-[[4-(3,4-dichlorophenoxy)-1-piperidinyl]methyl]-α-[(4-fluorophenyl)methyl]-1-piperidineacetate | 523/525 |
| 17 | (αS) Methyl α-[4-[[4-(3,4-dichlorophenoxy)-1-piperidinyl]methyl]-1-piperidinyl]-2-pyridinepropanoate | 506/508 |
| 18 | (αS) Methyl α-[(3-cyanophenyl)methyl]-4-[[4-(3,4-dichlorophenoxy)-1-piperidinyl]methyl]-1-piperidineacetate | 530/532 |
| 19 | (αS) Methyl α-[(2-cyanophenyl)methyl]-4-[[4-(3,4-dichlorophenoxy)-1-piperidinyl]methyl]-1-piperidineacetate | 530/532 |
| 20 | (αS) Methyl α-[4-[[4-(3,4-dichlorophenoxy)-1-piperidinyl]methyl]-1-piperidinyl]-4-pyridinepropanoate | 506/508 |
| 21 | (αS) Methyl 4-[[4-(3,4-dichlorophenoxy)-1-piperidinyl]methyl]-α-[(2-methoxyphenyl)methyl]-1-piperidineacetate | RT 2.22 (Fast) m/z 535/537 |
| 22 | (αS) Methyl α-[(2-cyanophenyl)methyl]-4-[[4-(3,4-dichloro-2-methylphenoxy)-1-piperidinyl]methyl]-1-piperidineacetate | RT 2.22 (Fast) m/z 544/546 |
| 23 | (αS) Methyl α-[(3-cyanophenyl)methyl]-4-[[4-(3,4-dichloro-2-methylphenoxy)-1-piperidinyl]methyl]-1-piperidineacetate | 530/532 |
| 24 | (αS) Methyl 4-[[4-(3,4-dichlorophenoxy)-1-piperidinyl]methyl]-α-[(4-methylphenyl)methyl]-1-piperidineacetate | 519/521 |
| 25 | (αS) Methyl 4-[[4-(3,4-dichlorophenoxy)-1-piperidinyl]methyl]-α-[(3-methylphenyl)methyl]-1-piperidineacetate | 519/521 |
| 26 | (αS) Methyl α-(4-cyanophenyl)methyl]-4-[[4-(3,4-dichlorophenoxy)-1-piperidinyl]methyl]-1-piperidineacetate | 530/532 |
| 27 | (αS) Methyl α-[(2-chlorophenyl)methyl]-4-[[4-(3,4-dichlorophenoxy)-1-piperidinyl]methyl]-1-piperidineacetate | RT (fast) 2.32 m/z 541/543 |
| 28 | (αS) Methyl 4-[[4-(3,4-dichlorophenoxy)-1-piperidinyl]methyl]-α-[[2-(trifluoromethyl)phenyl]methyl]-1-piperidineacetate | RT (fast) 2.58 m/z 573/575 |
| 29 | (αS) Methyl 4-[[4-(2,4-dichloro-3-methylphenoxy)-1-piperidinyl]methyl]-α-[(2-methoxyphenyl)methyl]-1-piperidineacetate | RT (fast) 2.31 m/z 549/551 |
| 30 | (αS) Methyl 4-[[4-(3,4-dichlorophenoxy)-1-piperidinyl]methyl]-α-(2-phenylethyl)-1-piperidineacetate | 519/521 |
| 31 | (±) (αS) Methyl 4-[[4-(3,4-dichlorophenoxy)-1-piperidinyl]methyl]-α-[(1S)-1-phenylethyl]-1-piperidineacetate<br>$^1$H NMR $\delta_{(CDCl3)}$ 0.66(1H, dd), 0.87(1H, dd), 1.17(3H, d), 1.25-1.36(1H, m), 1.52(4H, d), 1.66-1.77(2H, m), 1.87-1.95(2H, m), 2.00(2H, d), 2.13(1H, t), 2.26(1H, td), 2.53-2.62(2H, m), 2.68(1H, d), 2.87(1H, d), 3.17-3.26(1H, m), 3.32(1H, d), 3.73(3H, s), 4.16-4.23(1H, m), 6.72(1H, dd), 6.97(1H, d), 7.13-7.21(3H, m), 7.24-7.31(3H, m) | 519/521 |
| 33 | (αS) Methyl 4-[[4-(3-chloro-4-cyanophenoxy)-1-piperidinyl]methyl]-α-(phenylmethyl)-1-piperidineacetate<br>$^1$H NMR $\delta_{(CD3OD)}$ 1.15-1.31(2H, m), 1.53-1.66(1H, m), 1.72-1.89(4H, m), 2.00-2.10(2H, m), 2.23-2.49(6H, m), 2.75-2.85(2H, m), 2.93-3.07(4H, m), 3.40-3.45(1H, m), 3.53(3H, s), 4.55-4.63(1H, m), 7.04(1H, dd), 7.14-7.21(4H, m), 7.22-7.27(2H, m), 7.69(1H, d) | 496/498 |
| 34 | (αS) Methyl 4-[[4-(2-chloro-4-cyanophenoxy)-1-piperidinyl]methyl]-α-(phenylmethyl)-1-piperidineacetate<br>$^1$H NMR $\delta_{(CD3OD)}$ 1.75-1.90(4H, m), 2.07-2.16(2H, m), 2.18-2.29(2H, m), 2.35(1H, tm), 2.46(1H, td), 2.91-3.12(8H, m), 3.17-3.35(3H, m), 3.48(1H, dd), 3.56(3H, s), 4.88-4.95(1H, m), 7.14-7.20(3H, m), 7.22-7.27(2H, m), 7.33(1H, d), 7.67(1H, dd), 7.82(1H, d) | 496/498 RT 2.53 min Standard |
| 35 | (αS) Methyl 4-[[4-(4-chloro-2-methylphenoxy)-1-piperidinyl]methyl]-α-(phenylmethyl)-1-piperidineacetate<br>$^1$H NMR $\delta_{(CD3OD)}$ 1.14-1.29(2H, m), 1.50-1.62(1H, m), 1.72-1.85(4H, m), 1.95-2.03(2H, m), 2.18(3H, s), 2.23(2H, d), 2.26-2.38(4H, m), 2.65-2.73(2H, m), 2.92-3.06(4H, m), 3.42(1H, dd), 3.54(3H, s), 4.35-4.42(1H, m), 6.87(1H, d), 7.06-7.11(2H, m), 7.15-7.19(3H, m), 7.22-7.27(2H, m) | 485/487 |

TABLE II

| Example | Name | MS [M+H]+ (ES+) | $^1$H NMR |
|---|---|---|---|
| 38 | (αS)-4-[[4-(3,4-Dichlorophenoxy)-1-piperidinyl]methyl]-α-(phenylmethyl)-1-piperidineacetic acid | 491/493 | $\delta_{(CD3OD/NaOD)}$ 1.02-1.28(2H, m), 1.38-1.52(1H, m), 1.59-1.74(4H, m), 1.81-1.97(2H, m), 2.10-2.37(6H, m), 2.54-2.66(2H, m), 2.72(1H, dd), 2.86-3.06(3H, m), 3.07-3.17(1H, m), 4.24-4.32(1H, m), 6.78(1H, d), 6.97-7.20(6H, m), 7.27(1H, d) |
| 39 | (αR)-4-[[4-(3,4-Dichlorophenoxy)-1-piperidinyl]methyl]-α-(phenylmethyl)-1-piperidineacetic acid | 491/493 | $\delta_{(CD3OD/NaOD)}$ 1.06-1.28(2H, m), 1.41-1.51(1H, m), 1.60-1.74(4H, m), 1.84-1.95(2H, m), 2.11-2.36(6H, m), 2.54-2.66(2H, m), 2.68-2.76(1H, m), 2.87-3.04(3H, m), 3.08-3.16(1H, m), 4.24-4.33(1H, m), 6.78(1H, d), 6.98-7.19(6H, m), 7.27(1H, d) |
| 40 | (αS)-4-[[4-(3,4-Dichloro-2-methylphenoxy)-1-piperidinyl]methyl]-α-(phenylmethyl)-1-piperidineacetic acid | 505/507 | $\delta_{(CD3OD/NaOD)}$ 1.18-1.31(3H, m) 1.46-1.58(1H, m), 1.70-1.84(4H, m), 1.93-2.03(2H, m), 2.20(2H, d), 2.27(3H, s), 2.29-2.39(2H, m), 2.56-2.65(2H, m), 2.87(1H, dd), 2.97-3.15(5H, m), 4.36-4.44(1H, m), 6.88(1H, d), 7.09(1H, t), 7.18(2H, t), 7.21-7.27(3H, m) |
| 41 | (αS)-4-[[4-(3,4-Dichlorophenoxy)-1-piperidinyl]methyl]-α-[(2-methylphenyl)methyl]-1-piperidineacetic acid | 505/507 m pt 213° C. | $\delta_{(CD3OD/NaOD)}$ 1.18-1.37(3H, m), 1.49-1.63(1H, m), 1.71-1.81(4H, m), 1.95-2.04(2H, m), 2.25-2.27(2H, d), 2.29-2.40(4H, m), 2.33(3H, s), 2.64-2.74(2H, m) 2.89-3.04(3H, m), 3.05-3.22(3H, m), 4.38-4.42(1H, m), 6.91(1H, dd), 7.02-7.10(4H, m), 7.21-7.24(m, 1H), 7.40(1H, d) |

TABLE II-continued

| Example | Name | MS [M+H]+ (ES+) | 1H NMR |
|---|---|---|---|
| 42 | (αS)-α-[4-[[4-(3,4-Dichlorophenoxy)-1-piperidinyl]methyl]-1-piperidinyl]-3-pyridinepropanoic acid | 492/494 | δ$_{(CD3OD/NaOD)}$ 1.16-1.28(2H, m), 1.41-1.54(2H, m), 1.60-1.73(1H, m), 1.84-1.97(4H, m), 2.06-2.15(2H, m), 2.16-2.25(2H, m), 2.27-2.41(2H, m), 2.57-2.66(2H, m), 2.74-2.81(1H, m), 2.82-2.90(1H, m), 2.94-3.02(2H, m), 3.03-3.12(1H, m), 4.25-4.32(1H, m), 6.79(1H, dd), 7.00(1H, d), 7.19-7.23(1H, m), 7.27(1H, d), 7.64-7.68(1H, m), 8.20-8.23(1H, m), 8.34-8.35(1H, m) |
| 43 | (αS)-4-[[4-(3,4-Dichlorophenoxy)-1-piperidinyl]methyl]-α-[(2-fluorophenyl)methyl]-1-piperidineacetic acid | 509/511 | δ$_{(CD3OD)}$ 1.19-1.35(2H, m), 1.52-1.61(1H, m), 1.73-1.82(4H, m), 1.98-2.05(2H, m), 2.21-2.27(2H, m), 2.29-2.36(4H, m), 2.65-2.74(2H, m), 2.96(1H, m), 3.04-3.12(3H, m), 3.17-3.22(1H, m), 4.36-4.42(1H, m), 6.90(1H, d), 6.99(1H, t), 7.02-7.07(2H, m), 7.15-7.21(1H, m), 7.34(1H, t), 7.39(1H, d) |
| 44 | (αS)-4-[[4-(3,4-Dichlorophenoxy)-1-piperidinyl]methyl]-α-[[3-(trifluoromethyl)phenyl]methyl]-1-piperidineacetic acid | 559/561 | δ$_{(CD3OD/NaOD)}$ 1.18-1.39(2H, m), 1.51-1.65(1H, m), 1.71-1.85(4H, m), 1.95-2.09(2H, m), 2.24(2H, d), 2.28-2.47(4H, m), 2.66-2.77(2H, m), 2.95(1H, m), 2.99-3.14(3H, m), 3.15-3.20(1H, m), 4.34-4.45(1H, m), 6.90(1H, dd), 7.09(1H, d), 7.39(1H, d), 7.41-7.45(2H, m), 7.51-7.59(2H, m) |
| 45 | (αS)-α-[4-[[4-(3,4-Dichlorophenoxy)-1-piperidinyl]methyl]-1-piperidinyl]-1H-indole-3-propanoic acid | 530/532 | δ$_{(CD3OD/NaOD)}$ 1.14-1.50(2H, m), 1.52-1.70(1H, m), 1.71-1.89(4H, m), 1.95-2.09(2H, m), 2.22-2.56(6H, m), 2.67-2.81(2H, m), 2.92-3.30(5H, m), 4.35-4.46(1H, m), 6.87-7.15(5H, m), 7.26-7.31(1H, m), 7.39(1H, d), 7.62-7.66(1H, m) |
| 46 | (αS)-4-[[4-(3,4-Dichloro-2-methylphenoxy)-1-piperidinyl]methyl]-α-[(2-methylphenyl)methyl]-1-piperidineacetic acid | 517/519(M−H) | δ$_{(CD3OD)}$ 1.31(2H, dd), 1.57-1.66(1H, m), 1.77-1.90(4H, m), 1.99-2.09(2H, m), 2.28(2H, d), 2.34(3H, s), 2.35-2.47(4H, m), 2.39(3H, s), 2.66-2.76(2H, m), 2.94(1H, dd), 3.04-3.17(3H, m), 3.21(1H, dd), 4.42-4.50(1H, m), 6.95(1H, d), 7.03-7.12(3H, m), 7.25-7.28(1H, m), 7.31(1H, dd) |
| 47 | (αR)-4-[[4-(3,4-Dichloro-2-methylphenoxy)-1-piperidinyl]methyl]-α-(phenylmethyl)-1-piperidineacetic acid | 505/507 | δ$_{(CD3OD+1\ drop\ NaOD)}$ 1.16-1.40(2H, m), 1.52-1.66(1H, m), 1.73-1.88(4H, m), 1.96-2.08(2H, m), 2.25(2H, d), 2.30-2.45(8H, m), 2.63-2.74(2H, m), 2.85(1H, dd), 2.99-3.15(3H, m), 3.23(1H, dd), 4.38-4.48(1H, m), 6.93(1H, d), 7.09-7.31(6H, m) |
| 48 | (αR)-4-[[4-(3,4-Dichlorophenoxy)-1-piperidinyl]methyl]-α-[(2-methylphenyl)methyl]-1-piperidineacetic acid | 505/507 | δ$_{(CD3OD)}$ 1.18-1.40(2H, m), 1.51-1.66(1H, m), 1.71-1.85(4H, m), 1.95-2.07(2H, m), 2.22-2.48(9H, m), 2.67-2.78(2H, m), 2.91(1H, dd), 3.02-3.16(3H, m), 3.22(1H, dd), 4.34-4.45(1H, m), 6.90(1H, dd), 6.99-7.12(4H, m), 7.22-7.28(1H, m), 7.39(1H, d) |
| 49 | (αS)-4-[[4-(3,4-Dichlorophenoxy)-1-piperidinyl]methyl]-α-[(3-fluorophenyl)methyl]-1-piperidineacetic acid | 509/511(M+H) | δ$_{(CD3OD)}$ 1.18-1.35(2H, m), 1.51-1.61(1H, m), 1.69-1.82(4H, m), 1.95-2.04(2H, m), 2.23(2H, d), 2.27-2.35(2H, m), 2.39(2H, d), 2.65-2.74(2H, m), 2.81-2.88(1H, m), 2.97-3.11(3H, m), 3.15-3.20(1H, m), 4.33-4.42(1H, m), 6.81-6.90(2H, m), 7.00(1H, d), 7.05-7.09(2H, m), 7.21(1H, q), 7.37(1H, d) |
| 50 | (αS)-4-[[4-(3,4-Dichlorophenoxy)-1-piperidinyl]methyl]-α-[(4-fluorophenyl)methyl]-1-piperidineacetic acid | 507/509(M−H) | δ$_{(CD3OD)}$ 1.15-1.34(2H, m), 1.50-1.61(1H, m), 1.70-1.82(4H, m), 1.95-2.04(2H, m), 2.22(2H, d), 2.26-2.40(4H, m), 2.65-2.74(2H, m), 2.83(1H, dd), 3.04(3H, m), 3.10-3.15(3H, m), 4.34-4.42(1H, m), 6.86-6.95(3H, m), 7.07(1H, d), 7.25(2H, dd), 7.37(1H, d) |
| 51 | (αS)-α-[4-[[4-(3,4-Dichlorophenoxy)-1-piperidinyl]methyl]-1-piperidinyl]-2-pyridinepropanoic acid | 490/492(M−H) | δ$_{(CD3OD)}$ 1.05-1.32(2H, m), 1.49-1.60(1H, m), 1.69-1.80(4H, m), 1.95-2.03(2H, m), 2.21(2H, t), 2.26-240(4H, m), 2.55(1H, t), 2.64-2.73(2H, m), 2.97-3.11(3H, m), 3.17(1H, t), 4.33-4.42(1H, m), 6.88(1H, dd), 7.06(1H, d), 7.18-7.23(1H, m), 7.37(2H, d), 7.69(1H, t), 8.40(1H, d) |
| 52 | (αS)-α-[(3-Cyanophenyl)methyl]-4-[[4-(3,4-dichlorophenoxy)-1-piperidinyl]methyl]-1-piperidineacetic acid | 514/516(M−H) | δ$_{(CD3OD)}$ 1.17-1.41(2H, m), 1.53-1.67(1H, m), 1.73-1.88(4H, m), 1.97-2.09(2H, m), 2.26(2H, d), 2.37(4H, q), 2.67-2.79(2H, m), 2.92-3.21(5H, m), 4.35-4.47(1H, m), 6.91(1H, d), 7.11(1H, s), 7.37-7.50(2H, m), 7.55(1H, d), 7.59-7.68(2H, m) |
| 53 | (αS)-α-[(2-Cyanophenyl)methyl]-4-[[4-(3,4-dichlorophenoxy)-1-piperidinyl]methyl]-1-piperidineacetic acid | 514/516(M−H) | δ$_{(CD3OD)}$ 1.40-1.59(2H, m), 1.81-2.14(7H, m), 2.55(2H, d), 2.62-2.75(2H, m), 2.96(4H, t), 3.21-3.37(1H, m), 3.43-3.71(4H, m), 4.44-4.56(1H, m), 6.90-6.96(1H, m), 7.15(1H, t), 7.39-7.46(2H, m), 7.52-7.65(2H, m), 7.71(1H, d) |
| 54 | (αS)-α-[4-[[4-(3,4-Dichlorophenoxy)-1-piperidinyl]methyl]-1-piperidinyl]-4-pyridinepropanoic acid | 492/494(M+H) | δ$_{(DMSO)}$ 0.93-1.05(2H, m), 1.38-1.47(1H, m), 1.50-1.69(4H, m), 1.83-1.91(2H, m), 2.07(2H, d), 2.09-2.26(4H, m), 2.54-2.66(2H, m), 2.74-2.99(5H, m), 4.35-4.44(1H, m), 6.95(1H, dd), 7.20-7.25(3H, m), 7.47(1H, d), 8.40(2H, d) |
| 55 | (αS)-4-[[4-(3,4-Dichlorophenoxy)-1-piperidinyl]methyl]-α-[(2-methoxyphenyl)methyl]-1-piperidineacetic acid | 521/523(M+H) | δ$_{(CD3OD)}$ 1.16-1.36(2H, m), 1.50-1.61(1H, m), 1.69-1.81(4H, m), 1.94-2.03(2H, m), 2.22(2H, d), 2.26-2.41(4H, m), 2.65-2.74(2H, m), 2.87(1H, dd), 3.01-3.13(3H, m), 3.26(1H, dd), 3.80(3H, s), 4.33-4.41(1H, m), 6.77(1H, d), 6.83-6.89(2H, m), 7.07(1H, d), 7.11(1H, td), 7.20(1H, d), 7.36(1H, d) |
| 56 | (αS)-α-[(2-Cyanophenyl)methyl]-4-[[4-(3,4-dichloro-2-methylphenoxy)-1-piperidinyl]methyl]-1-piperidineacetic acid | 528/530(M−H) | δ$_{(CD3OD)}$ 1.18-1.31(2H, m), 1.49-1.62(1H, m), 1.70-1.85(4H, m), 1.95-2.04(2H, m), 2.21(2H, d), 2.29(3H, s), 2.31-2.44(4H, m), 2.60-2.71(2H, m), 3.01-3.25(5H, m), 4.36-4.46(1H, m), 6.90(1H, d), 7.26(1H, d), 7.33(1H, t), 7.47-7.56(2H, m), 7.62(1H, d) |
| 57 | (αS)-α-[(3-Cyanophenyl)methyl]-4-[[4-(3,4-dichloro-2-methylphenoxy)-1-piperidinyl]methyl]-1-piperidineacetic acid | 528/530(M−H) | δ$_{(CD3OD)}$ 1.15-1.33(2H, m), 1.50-1.61(1H, m), 1.71-1.85(4H, m), 1.94-2.04(2H, m), 2.22(2H, d), 2.28(3H, s), 2.31-2.39(4H, m), 2.58-2.70(2H, m), 2.89-3.15(5H, m), 4.36-4.46(1H, m), 6.90(1H, d), 7.26(1H, d), 7.42(1H, t), 7.51(1H, d), 7.58(1H, d), 7.61(1H, s) |

TABLE II-continued

| Example | Name | MS [M+H]⁺ (ES+) | ¹H NMR |
|---|---|---|---|
| 58 | (αS)-4-[[4-(3,4-Dichlorophenoxy)-1-piperidinyl]methyl]-α-[(R)-hydroxyphenylmethyl]-1-piperidineacetic acid | 507/509(M+H) | δ$_{(CD3OD)}$ 1.19-1.44(2H, m), 1.55-1.67(1H, m), 1.75-1.90(4H, m), 1.99-2.08(2H, m), 2.25-2.40(5H, m), 2.75(3H, t), 2.91(1H, d), 3.10-3.19(2H, m), 4.37-4.46(1H, m), 4.84(1H, d), 6.92(1H, dd), 7.11(1H, d), 7.21-7.26(1H, m), 7.30(2H, t), 7.41(1H, d), 7.49(2H, d) |
| 59 | (αS)-4-[[4-(3,4-Dichlorophenoxy)-1-piperidinyl]methyl]-α-[(1S)-1-phenylethyl]-1-piperidineacetic acid | 503/505(M−H) | δ$_{(CD3OD)}$ 0.84-0.96(1H, m), 1.15-1.44(6H, m), 1.73-1.93(5H, m), 1.96-2.11(2H, m), 2.35(2H, d), 2.43-2.55(2H, m), 2.75-2.86(3H, m), 2.89-3.12(1H, m), 3.35-3.58(1H, m), 3.68(1H, d), 4.39-4.50(1H, m), 6.91(1H, dd), 7.12(1H, d), 7.22-7.30(1H, m), 7.32-7.42(5H, m) |
| 60 | (αS)-4-[[4-(3,4-Dichlorophenoxy)-1-piperidinyl]methyl]-α-[(4-methylphenyl)methyl]-1-piperidineacetic acid | (APCI) 503/505[M−H]⁺ | δ$_{(CD3OD)}$ 1.14-1.34(2H, m), 1.49-1.61(1H, m), 1.69-1.82(4H, m), 1.94-2.03(2H, m), 2.19-2.34(4H, m), 2.24(3H, s), 2.37(2H, q), 2.66-2.73(2H, m), 2.76(1H, dd), 2.96-3.09(3H, m), 3.17(1H, dd), 4.33-4.41(1H, m), 6.87(1H, dd), 7.00(2H, d), 7.08(1H, d), 7.13(2H, d), 7.36(1H, d) |
| 61 | (αS)-4-[[4-(3,4-Dichlorophenoxy)-1-piperidinyl]methyl]-α-[(3-methylphenyl)methyl]-1-piperidineacetic acid | (APCI) 503/505[M−H]⁺ | δ$_{(CD3OD)}$ 1.17-1.41(2H, m), 1.51-1.65(1H, m), 1.72-1.85(4H, m), 1.96-2.07(2H, m), 2.25(2H, d), 2.29(3H, s), 2.31-2.46(4H, m), 2.67-2.77(2H, m), 2.81(1H, dd), 3.06(3H, t), 3.21(1H, dd), 4.34-4.46(1H, m), 6.88-6.98(2H, m), 7.04-7.13(4H, m), 7.39(1H, d) |
| 62 | (αS)-α-[(4-Cyanophenyl)methyl]-4-[[4-(3,4-dichlorophenoxy)-1-piperidinyl]methyl]-1-piperidineacetic acid, | (APCI) 516/518[M+H]⁺ | δ$_{(CD3OD)}$ 1.15-1.43(2H, m), 1.50-1.66(1H, m), 1.71-1.86(4H, m), 1.96-2.08(1H, m), 2.24(2H, d), 2.27-2.48(4H, m), 2.66-2.80(2H, m), 2.90-3.25(5H, m), 4.33-4.45(1H, m), 6.90(1H, d), 7.10(1H, s), 7.39(1H, d), 7.47(2H, d), 7.60(2H, d) |
| 63 | (αS)-α-[(2-Chlorophenyl)methyl]-4-[[4-(3,4-dichlorophenoxy)-1-piperidinyl]methyl]-1-piperidineacetic acid | (APCI) 525/527/529[M−H]⁺ | δ$_{(CD3OD)}$ 1.19-1.35(2H, m), 1.49-1.61(1H, m), 1.71-1.82(4H, m), 1.94-2.05(2H, m), 2.22(2H, d), 2.33(4H, q), 2.65-2.73(2H, m), 2.97-3.27(5H, m), 4.32-4.42(1H, m), 6.88(1H, dd), 7.06(1H, d), 7.10-7.18(2H, m), 7.27-7.31(1H, m), 7.37(2H, d) |
| 64 | (αS)-4-[[4-(3,4-Dichlorophenoxy)-1-piperidinyl]methyl]-α-[[2-(trifluoromethyl)phenyl]methyl]-1-piperidineacetic acid | (APCI) 559/561[M+H]⁺ | δ$_{(CD3OD)}$ 1.19-1.45(2H, m), 1.67-1.81(3H, m), 1.86-1.98(4H, m), 2.30(2H, d), 2.34-2.46(2H, m), 2.68-2.77(2H, m), 2.84(2H, q), 3.08-3.16(1H, m), 3.31-3.54(4H, m), 4.30-4.38(1H, m), 6.80(1H, dd), 7.01(1H, d), 7.27-7.34(2H, m), 7.45(2H, q), 7.57(1H, d) |
| 65 | (αS)-4-[[4-(2,4-Dichloro-3-methylphenoxy)-1-piperidinyl]methyl]-α-[(2-methoxyphenyl)methyl]-1-piperidineacetic acid | (APCI) 533/535[M−H]⁺ | δ$_{(CD3OD)}$ 1.17-1.41(2H, m), 1.50-1.66(1H, m), 1.72-1.90(4H, m), 1.93-2.06(2H, m), 2.24(2H, d), 2.31-2.42(4H, m), 2.44(3H, s), 2.64-2.77(2H, m), 2.88(1H, t), 3.00-3.15(4H, m), 3.82(3H, s), 4.40-4.51(1H, m), 6.78(1H, t), 6.86(1H, d), 6.94(1H, d), 7.12(1H, t), 7.23(2H, t) |
| 66 | (αS)-4-[[4-(3,4-Dichlorophenoxy)-1-piperidinyl]methyl]-α-(2-phenylethyl)-1-piperidineacetic acid | 503/505(M−H) | δ$_{(CD3OD/NaOD)}$ 1.25(2H, dd), 1.49-1.59(1H, m), 1.70-1.80(4H, m), 1.81-1.91(1H, m), 1.94-2.03(3H, m), 2.19-2.34(6H, m), 2.51-2.61(1H, m), 2.63-2.73(3H, m), 2.90(1H, dd), 2.94-3.04(2H, m), 4.32-4.42(1H, m), 6.87(1H, dd), 7.06(1H, d), 7.12(1H, dt), 7.18-7.25(4H, m), 7.36(1H, d). |
| 67 | (αS)-4-[[4-[(4-Fluorophenyl)methyl]-1-piperidinyl]methyl]-α-(phenylmethyl)-1-piperidineacetic acid | MS 439[M+H]+ (ES+). Retention time: 1.35 Standard | δ$_{(CD3OD)}$ 1.21-1.39(4H, m), 1.49-1.57(2H, m), 1.58-1.65(2H, m), 1.73-1.81(2H, m), 1.89(2H, t), 2.20(2H, d), 2.28-2.41(2H, m), 2.54(2H, d), 2.86-2.93(3H, m), 3.03-3.12(3H, m), 3.19(1H, dd), 7.00(2H, t), 7.12-7.20(3H, m), 7.21-7.26(2H, m), 7.27-7.31(2H, m). |
| 68 | (αS)-4-[[4-(2-Chloro-4-cyanophenoxy)-1-piperidinyl]methyl]-α-(phenylmethyl)-1-piperidineacetic acid | 480/482[M−H] APCI- | δ$_{(CD3OD)}$ 1.16-1.39(2H, m), 1.50-1.66(1H, m), 1.74-1.87(4H, m), 1.99-2.10(2H, m), 2.26(2H, d), 2.30-2.46(4H, m), 2.68-2.77(2H, m), 2.85(1H, m), 3.00-3.15(3H, m), 3.23(1H, dd), 4.52-4.61(1H, m), 7.05(1H, dd), 7.10-7.17(1H, m), 7.19-7.31(5H, m), 7.71(1H, d) |
| 69 | (αS)-4-[[4-(2-Chloro-4-cyanophenoxy)-1-piperidinyl]methyl]-α-(phenylmethyl)-1-piperidineacetic acid | 482/484[M+H]+ (ES+). | δ$_{(DMSO)}$ 0.99-1.13(2H, m), 1.41-1.52(1H, m), 1.61-1.73(3H, m), 1.87-1.97(2H, m), 2.11(2H, d), 2.21-2.30(3H, m), 2.39-2.47(2H, m), 2.54-2.61(1H, m), 2.78-2.89(2H, m), 2.92-3.03(2H, m), 3.30-3.39(2H, m), 4.64-4.73(1H, m), 7.14-7.28(5H, m), 7.38(1H, d), 7.77(1H, dd), 8.01(1H, d). |
| 70 | (αS)-4-[[4-(4-Chloro-2-methylphenoxy)-1-piperidinyl]methyl]-α-(phenylmethyl)-1-piperidineacetic acid | 471/473 | δ$_{(CD3OD)}$ 1.16-1.35(2H, m), 1.50-1.63(1H, m), 1.72-1.84(4H, m), 1.95-2.03(2H, m), 2.17(3H, s), 2.23(2H, d), 2.30-2.42(4H, m), 2.63-2.72(2H, m), 2.83(1H, dd), 2.98-3.11(3H, m), 3.20(1H, m), 4.34-4.41(1H, m), 6.87(1H, d), 7.05-7.13(3H, m), 7.20(2H, t), 7.26(2H, d) |
| 72 | (αS)-4-[[4-(3,4-Dichlorophenoxy)-1-piperidinyl]methyl]-α-(phenylmethyl)-1-piperidineacetic acid dihydrochloride | 491/493 | δ$_{(CD3OD/NaOD)}$ 1.05-1.26(2H, m), 1.41-1.54(1H, m), 1.61-1.73(4H, m), 1.85-1.94(2H, m), 2.07-2.16(2H, m), 2.16-2.25(2H, m), 2.26-2.35(2H, m), 2.57-2.65(2H, m), 2.72(1H, dd), 2.87-2.94(1H, m), 2.95-3.05(2H, m), 3.10-3.16(1H, m), 4.24-4.33(1H, m), 6.76-6.81(1H, m), 6.98-7.04(2H, m), 7.10(2H, t), 7.17(2H, d), 7.27(1H, dd) |
| 73 | (αS)-4-[[4-(3,4-Dichloro-2-methylphenoxy)-1-piperidinyl]methyl]-α-(phenylmethyl)-1-piperidineacetic acid dihydrochloride | 505/507 | δ$_{(CD3OD)}$ 1.56-1.69(2H, m), 1.92-2.02(1H, m), 2.05-2.25(6H, m), 2.31(3H, s), 3.07-3.15(4H, m), 3.14-3.27(2H, m), 3.39(1H, dd), 3.44-3.52(2H, m), 3.53-3.60(2H, m), 3.60-3.68(1H, m), 3.71-3.81(1H, m), 4.12-4.21(1H, m), 6.86-6.96(1H, m), 7.17-7.29(6H, m) |

TABLE II-continued

| Example | Name | MS [M+H]+ (ES+) | $^1$H NMR |
|---|---|---|---|
| 74 | (αS)-α-[(4-Chlorophenyl)methyl]-4-[[4-(3,4-dichlorophenoxy)-1-piperidinyl]methyl]-1-piperidineacetic acid dihydrochloride | (APCI) 525/ 531[M+H]+ | $\delta_{(CD3OD)}$ 1.55-1.71(2H, m), 1.88-2.00(1H, m), 2.03-2.33(6H, m), 3.04-3.15(4H, m), 3.16-3.30(3H, m), 3.34-3.48(3H, m), 3.52-3.59(1H, m), 3.60-3.67(1H, m), 3.70-3.78(1H, m), 4.11-4.19(1H, m), 6.83-6.94(1H, m), 7.09-7.17(1H, m), 7.24(4H, q), 7.34(1H, d) |
| 75 | (αS)-4-[[4-(3,4-Dichlorophenoxy)-1-piperidinyl]methyl]-α-[(2-methylphenyl)methyl]-1-piperidineacetic acid, dihydrochloride | (APCI) 505/ 509[M+H]+ | $\delta_{(CD3OD)}$ 1.56-1.74(2H, m), 1.88-1.99(1H, m), 2.05-2.27(6H, m), 2.30(3H, s), 3.05-3.15(4H, m), 3.15-3.33(3H, m), 3.36-3.49(3H, m), 3.54-3.69(2H, m), 3.78-3.88(1H, m), 4.04-4.13(1H, m), 6.84-6.94(1H, m), 7.00-7.18(5H, m), 7.34(1H, d) |
| 76 | (αS)-4-[[4-(3,4-Dichlorophenoxy)-1-piperidinyl]methyl]-α-[(4-methoxyphenyl)methyl]-1-piperidineacetic acid dihydrochloride | (APCI) 521/ 525[M+H]+ | $\delta_{(DMSO)}$ 1.55-1.72(2H, m), 1.93-2.33(7H, m), 2.93-3.17(6H, m), 3.31-3.52(4H, m), 3.54-3.64(2H, m), 3.73(3H, s), 4.02-4.16(1H, m), 4.79-4.86(1H, m), 6.89(2H, d), 7.06(1H, t), 7.18(2H, d), 7.32-7.40(1H, m), 7.56(1H, t) |
| 77 | (αR)-4-[[4-(3,4-Dichlorophenoxy)-1-piperidinyl]methyl]-α-[(2-methylphenyl)methyl]-1-piperidineacetic acid dihydrochloride | 505/507 | $\delta_{(CD3OD)}$ 1.66-1.88(2H, m), 1.97-2.43(10H, m), 3.16-3.27(6H, m), 3.37-3.49(2H, m), 3.51-3.61(3H, m), 3.66-3.79(2H, m), 4.17-4.26(1H, m), 6.95-7.06(1H, m), 7.13-7.30(5H, m), 7.43-7.50(1H, m) |
| 78 | (αS)-4-[[4-(3,4-Dichlorophenoxy)-1-piperidinyl]methyl]-α-(2-phenylethyl)-1-piperidineacetic acid dihydrochloride | 503/ 505[M−H] | $\delta_{(CD3OD)}$ 1.63-1.78(2H, m), 1.97-2.09(1H, m), 2.11-2.40(8H, m), 2.69-2.79(1H, m), 2.83-2.93(1H, m), 3.13-3.22(4H, m), 3.32-3.38(1H, m), 3.48-3.57(3H, m), 3.64-3.77(2H, m), 3.95-4.03(1H, m), 4.80(1H, s), 7.00(1H, dd), 7.19-7.34(6H, m), 7.43(1H, dd) |
| 81 | (αS)-4-[[4-(3,4-Dichlorophenoxy)-1-piperidinyl]methyl]-α-[(1-methyl-1H-imidazol-5-yl)methyl]-1-piperidineacetic acid | 495/497 | δ(CD$_3$OD/NaOD) 1.23-1.37(4H, m), 1.50-1.64(2H, m), 1.70-1.84(4H, m), 1.92-2.05(2H, m), 2.15-2.26(2H, m), 2.26-2.50(3H, m), 2.63-2.82(2H, m), 2.96-3.10(2H, m), 3.20-3.27(1H, m), 3.65(3H, s), 4.34-4.41(1H, m), 6.79(1H, s), 6.88(1H, dd), 7.08(1H, d), 7.37(1H, d), 7.46(1H, s) |

EXAMPLE 84

Pharmacological Analysis: Calcium Flux [Ca$^{2+}$]$_i$ Assay

Human Eosinophils

Human eosinophils were isolated from EDTA anticoagulated peripheral blood as previously described (Hansel et al., *J. Immnunol. Methods*, 1991, 145, 105-110). The cells were resuspended (5×10$^6$ mL$^{-1}$) and loaded with 5 µM FLUO-3/AM+Pluronic F127 2.2 µl/mL (Molecular Probes) in low potassium solution (LKS; NaCl 118 mM, MgSO$_4$ 0.8 mM, glucose 5.5 mM, Na$_2$CO$_3$ 8.5 mM, KCl 5 mM, HEPES 20 mM, CaCl$_2$ 1.8 mM, BSA 0.1%, pH 7.4) for one hour at room temperature. After loading, cells were centrifuged at 200×g for 5 min and resuspended in LKS at 2.5×10$^6$ mL$^{-1}$. The cells were then transferred to 96 well FLIPr plates (Poly-D-Lysine plates from Becton Dickinson pre-incubated with 50 µM. fibronectin for two hours) at 25 µl/well. The plate was centrifuged at 200 g for 5 min and the cells were washed twice with LKS (200 µl; room temperature).

A compound of the Examples was pre-dissolved in DMSO and added to a final concentration of 0.1% (v/v) DMSO. Assays were initiated by the addition of an A$_{50}$ concentration of eotaxin and the transient increase in fluo-3 fluorescence (1$_{Ex}$=490 nm and 1$_{Em}$=520 nm) monitored using a FLIPR (Fluorometric Imaging Plate Reader, Molecular Devices, Sunnyvale, U.S.A.).

Compounds of the Examples were found to be antagonists if the increase in fluorescence induced by eotaxin (a selective CCR3 agonist) was inhibited in a concentration dependent manner. The concentration of antagonist required to inhibit the fluorescence by 50% can be used to determine the IC$_{50}$ for the antagonist at the CCR3 receptor.

EXAMPLE 85

Human Eosinophil Chemotaxis

Human eosinophils were isolated from EDTA anticoagulated peripheral blood as previously described (Hansel et al., *J. Immunol. Methods*, 1991, 145, 105-110). The cells were resuspended at 10×10$^6$ mL$^{-1}$ in RPMI containing 200 IU/mL penicillin, 200 µg /mL streptomycin sulfate and supplemented with 10% HIFCS, at room temperature.

Eosinophils (700 µl) were pre-incubated for 15 rains at 37° C. with 7 µl of either vehicle or compound (100× required final concentration in 10% DMSO). The chemotaxis plate (ChemoTx, 3 µm pore, Neuroprobe) was loaded by adding 28 µl of a concentration of eotaxin 0.1 to 100 nm (a selective CCR3 agonist over this concentration range) containing a concentration of a compound according to the Examples or solvent to the lower wells of the chemotaxis plate. The filter was then placed over the wells and 25 µl of eosinophil suspension were added to the top of the filter. The plate was incubated for 1 hr at 37° C. in a humidified incubator with a 95% air/5% CO$_2$ atmosphere to allow chemotaxis.

The medium, containing cells that had not migrated, was carefully aspirated from above the filter and discarded. The filter was washed once with phosphate buffered saline PBS) containing 5 mM EDTA to remove any adherent cells. Cells that had migrated through the filter were pelleted by centrifugation (300×g for 5 mins at room temperature) and the filter removed and the supernatant transferred to each well of a 96-well plate (Costar). The pelleted cells were lysed by the addition of 28 µl of PBS containing 0.5% Triton×100 followed by two cycles of freeze/thawing. The cell lysate was then added to the supernatant. The number of eosinophils migrating was quantified according to the method of Strath et al., *J. Immunol. Methods*, 1985, 83, 209 by measuring eosinophil peroxidase activity in the supernatant.

Compounds of the Examples were found to be antagonists of eotaxin mediated human eosinophil chemotaxis if the concentration response to eotaxin was shifted to the right of the control curve. Measuring the concentration of eotaxin required to give 50% chemotaxis in the presence or absence of compounds enables the apparent affinity of the compounds at CCR3 to be calculated.

EXAMPLE 86

Guinea-Pig Isolated Trachea (See for example, Harrison, R. W. S., Carswell, H. & Young, J. M. (1984) European J. Pharmacol., 106, 405-409.)

Male albino Dunkin-Hartley guinea-pigs (250 g) were killed by cervical dislocation and the whole trachea removed. After clearing the adherent connective tissue, the trachea was cut into six ring segments each three cartilage bands wide and then suspended in 20 mL organ baths containing Krebs-Henseleit solution of the following composition (mM): NaCl 117.6, $NaH_2PO_4$ 0.9, $NaHCO_3$ 25.0, $MgSO_4$ 1.2, KCl 5.4, $CaCl_2$ 2.6 and glucose 11.1. The buffer was maintained at 37° C. and gassed with 5% $CO_2$ in oxygen. Indomethacin (2.8 µM was added to the Krebs solution to prevent development of smooth muscle tone due to the synthesis of cyclo-oxygenase products. The tracheal rings were suspended between two parallel tungsten wire hooks, one attached to an Ormed beam isometric force transducer and the other to a stationary support in the organ bath. Changes in isometric force were recorded on 2-channel Sekonic flat bed chart recorders.

Experimental Protocols

At the beginning of each experiment a force of 1 g was applied to the tissues and this was reinstated over a 60 minute equilibration period until a steady resting tone was achieved Subsequently, a cumulative histamine concentration effect (E/[A]) curve was constructed at 0.5 $\log_{10}$ unit increments, in each tissue. The tissues were then washed and approximately 30 minutes later, test compound or vehicle (20% DMSO) was added. Following an incubation period of 60 minutes a second E/[A] curve was performed to histamine.

Contraction responses were recorded as a percentage of the first curve maximum.

Data Analysis

Experimental E/[A] curve data were analysed for the purposes of estimating the potencies ($p[A_{50}]$ values) of histamine in the absence and presence of the test compound. Affinity ($pA_2$) values of test compounds were subsequently calculated using the following equation:

$$\log(r-1) = \log[B] + pA_2$$

where $r = [A]_{50}$ in presence of test compound/$[A]_{50}$ in absence of antagonist and [B] is the concentration of test compound. Compounds of the Examples were found to be H1 antagonists.

EXAMPLE 87

Histamine H1 receptor binding activity of compounds of the invention was assessed by competition displacement of 1 nM [3H]-pyrlamine (Amersham, Bucks, Product code TRK 608, specific activity 30 Ci/mmol) to 2 µg membranes prepared from recombinant CHO-K1 cells expressing the human H1 receptor (Euroscreen SA, Brussels, Belgium, product code ES-390-M) in assay buffer (50 mM Tris pH 7.4 containing 2 mM $MgCl_2$, 250 mM sucrose and 100 nM NaCl) for 1 hour at room temperature.

The following compounds of the invention gave inhibition of [3H] pyrilimine binding:

| Example | H1 pKi |
|---------|--------|
| 37 | 7.5 |
| 38 | 7.5 |
| 39 | 7.0 |
| 40 | 7.0 |
| 41 | 7.7 |
| 45 | 7.0 |
| 42 | 7.3 |
| 43 | 7.3 |
| 44 | 6.8 |
| 50 | 7.5 |
| 53 | 8.0 |
| 56 | 7.9 |
| 57 | 7.7 |
| 58 | 6.9 |
| 59 | 7.2 |
| 66 | 7.2 |
| 71 | 6.8 |
| 72 | 7.2 |
| 73 | 7.2 |
| 74 | 7.5 |
| 78 | 6.9 |
| 80 | 6.6 |
| 81 | 6.4 |

The invention claimed is:
1. A compound of formula (I):

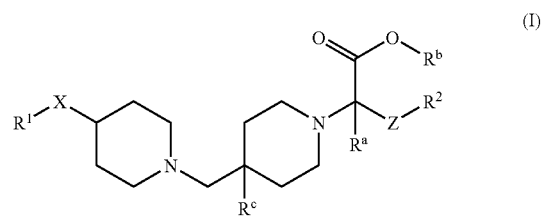

wherein:
$R^a$ and $R^b$ are, independently, hydrogen or $C_{1-4}$ alkyl;
$R^c$ is hydrogen or hydroxy;
X is $CH_2$, C(O), O, S, S(O), $S(O)_2$ or $NR^3$;
Z is $CHR^d(CH_2)_n$;
n is 0 or 1;
$R^d$ is hydrogen, $C_{1-4}$ alkyl, hydroxy or $C_{1-4}$ alkoxy;
$R^1$ is hydrogen, $C_{1-6}$ alkyl, aryl or heterocyclyl;
$R^2$ is aryl or heterocyclyl;
wherein, unless stated otherwise, the foregoing aryl and heterocyclyl moieties are optionally substituted by: halogen, cyano, nitro, hydroxy, oxo, $S(O)_pR^4$, $OC(O)NR^5R^6$, $NR^7R^8$, $NR^9C(O)R^{10}$, $NR^{11}C(O)NR^{12}R^{13}$, $S(O)_2NR^{14}R^{15}$, $NR^{16}S(O)_2R^{17}$, $C(O)NR^{18}R^{19}$, $C(O)R^{20}$, $CO_2R^{21}$, $NR^{22}CO_2R^{23}$, $C_{1-6}$ alkyl, $CF_3$, $C_{1-6}$ alkoxy($C_{1-6}$)alkyl, $C_{1-6}$ alkoxy, $OCF_3$, $C_{1-6}$ alkoxy($C_{1-6}$) alkoxy, $C_{1-6}$ alkylthio, $C_{2-6}$ alkenyl, $C_{2-6}$ alkynyl, $C_{3-10}$ cycloalkyl (itself optionally substituted by $C_{1-4}$ alkyl or oxo), methylenedioxy, difluoromethylenedioxy, phenyl, phenyl($C_{1-4}$alkyl, phenoxy, phenylthio, phenyl($C_{1-4}$ alkoxy, heterocyclyl, heterocyclyl($C_{1-4}$alkyl, heterocyclyloxy or heterocyclyl($C_{1-4}$)alkoxy; wherein any of the immediately foregoing phenyl and heterocyclyl moieties are optionally substituted with halogen, hydroxy, nitro, $S(O)_q(C_{1-4}$ alkyl), $S(O)_2NH_2$, $S(O)_2NH(C_{1-4}$ alkyl), $S(O)_2N(C_{1-4}$ alkyl)$_2$ (and these alkyl groups optionally join to form a ring as described for $R^5$ and $R^6$ below), cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$ (and these alkyl groups optionally join to form a ring as described for $R^5$ and $R^6$ below), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$;

p and q are, independently, 0, 1 or 2;

$R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$ and $R^{22}$ are, independently, hydrogen, $C_{1-6}$ alkyl (optionally substituted by halogen, hydroxy or $C_{3-10}$ cycloalkyl), $CH_2(C_{2-6}$ alkenyl), phenyl (itself optionally substituted by halogen, hydroxy, nitro, $NH_2$, $NH(C_{1-4}$ alkyl), $N(C_{1-4}$ alkyl)$_2$ (and these alkyl groups optionally join to form a ring as described for $R^5$ and $R^6$ below), $S(O)_2(C_{1-4}$ alkyl), $S(O)_2NH_2$, $S(O)_2NH(C_{1-4}$ alkyl), $S(O)_2N(C_{1-4}$ alkyl)$_2$ (and these alkyl groups optionally join to form a ring as described for $R^5$ and $R^6$ below), cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$ (and these alkyl groups optionally join to form a ring as described for $R^5$ and $R^6$ below), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$) or heterocyclyl (itself optionally substituted by halogen, hydroxy, nitro, $NH_2$, $NH(C_{1-4}$ alkyl), $N(C_{1-4}$ alkyl)$_2$ (and these alkyl groups optionally join to form a ring as described for $R^5$ and $R^6$ below), $S(O)_2(C_{1-4}$ alkyl), $S(O)_2NH_2$, $S(O)_2NH(C_{1-4}$ alkyl), $S(O)_2N(C_{1-4}$ alkyl)$_2$ (and these alkyl groups optionally join to form a ring as described for $R^5$ and $R^6$ below), cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$ (and these alkyl groups optionally join to form a ring as described for $R^5$ and $R^6$ below), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$);

alternatively $NR^5R^6$, $NR^7R^8$, $NR^{12}R^{13}$, $NR^{14}R^{15}$, $NR^{18}R^{19}$, independently, form a 4-7 membered heterocyclic ring, azetidine, pyrrolidine, piperidine, azepine, morpholine or piperazine, the latter optionally substituted by $C_{1-4}$ alkyl on the distal nitrogen;

$R^4$, $R^{17}$ and $R^{23}$ are, independently, $C_{1-6}$ alkyl (optionally substituted by halogen, hydroxy or $C_{3-10}$ cycloalkyl), $CH_2(C_{2-6}$ alkenyl), phenyl (itself optionally substituted by halogen, hydroxy, nitro, $NH_2$, $NH(C_{1-4}$ alkyl), $N(C_{1-4}$ alkyl)$_2$ (and these alkyl groups optionally join to form a ring as described for $R^5$ and $R^6$ above), $S(O)_2(C_{1-4}$ alkyl), $S(O)_2NH_2$, $S(O)_2NH(C_{1-4}$ alkyl), $S(O)_2N(C_{1-4}$ alkyl)$_2$ (and these alkyl groups optionally join to form a ring as described for $R^5$ and $R^6$ above), cyano, $C_{1-4}$ alkyl, $C_{1-4}$ alkoxy, $C(O)NH_2$, $C(O)NH(C_{1-4}$ alkyl), $C(O)N(C_{1-4}$alkyl)$_2$ (and these alkyl groups optionally join to form a ring as described for $R^5$ and $R^6$ above), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$) or heterocyclyl (itself optionally substituted by halogen, hydroxy, nitro, $NH_2$, $NH(C_{1-4}$ alkyl), $N(C_{1-4}$ alkyl)$_2$ (and these alkyl groups optionally join to form a ring as described for $R^5$ and $R^6$ above), $S(O)_2(C_{1-4}$ alkyl), $S(O)_2NH_2$, $S(O)_2NH(C_{1-4}$ alkyl), $S(O)_2N(C_{1-4}$ alkyl)$_2$ (and these alkyl groups optionally join to form a ring as described for $R^5$ and $R^6$ above), cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$ (and these alkyl groups optionally join to form a ring as described for $R^5$ and $R^6$ above), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$);

$R^3$ is hydrogen, $C_{1-6}$ alkyl or benzyl;

or an N-oxide thereof; or a pharmaceutically acceptable salt thereof.

2. A compound of formula (I) as claimed in claim 1 wherein X is O.

3. A compound of formula (I) as claimed in claim 1 wherein the aryl and heterocyclyl moieties of $R^1$ and $R^2$ are, independently, optionally substituted by: halogen, cyano, nitro, hydroxy, oxo, $S(O)_pR^4$, $OC(O)NR^5R^6$, $NR^7R^8$, $NR^9C(O)R^{10}$, $NR^{11}C(O)NR^{12}R^{13}$, $S(O)_2NR^{14}R^{15}$, $NR^{16}S(O)_2R^{17}$, $C(O)NR^{18}R^{19}$, $C(O)R^{20}$, $CO_2R^{21}$, $NR^{22}CO_2R^{23}$, $C_{1-6}$ alkyl, $CF_3$, $C_{1-6}$ alkoxy($C_{1-6}$)alkyl, $C_{1-6}$ alkoxy or $OCF_3$; p is 0, 1 or 2; $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$ and $R^{22}$ are, independently, hydrogen, $C_{1-6}$ alkyl (optionally substituted by halogen) or phenyl (itself optionally substituted by halogen, hydroxy, nitro, $NH_2$, $NH(C_{1-4}$ alkyl), $N(C_{1-4}$ alkyl)$_2$, $S(O)_2(C_{1-4}$ alkyl), $S(O)_2NH_2$, $S(O)_2NH(C_{1-4}$ alkyl), $S(O)_2N(C_{1-4}$ alkyl)$_2$, cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$, $CO_2H$, $CO_2(C_{1-4}$ alkyl), $NHC(O)(C_{1-4}$ alkyl), $NHS(O)_2(C_{1-4}$alkyl), $C(O)(C_{1-4}$ alkyl), $CF_3$ or $OCF_3$); and $R^4$, $R^{17}$ and $R^{23}$ are, independently, $C_{1-6}$ alkyl (optionally substituted by halogen) or phenyl (itself optionally substituted by halogen, hydroxy, nitro, $NH_2$, $NH(C_{1-4}$ alkyl), $N(C_{1-4}$ alkyl)$_2$, $S(O)_2(C_{1-4}$ alkyl), $S(O)_2NH_2$, $S(O)_2NH(C_{1-4}$ alkyl), $S(O)_2N(C_{1-4}$ alkyl)$_2$, cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$, $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$).

4. A compound of formula (I) as claimed in claim 1 wherein $R^1$ is phenyl optionally substituted with halogen, cyano, $C_{1-4}$ alkyl or $C_{1-4}$ alkoxy.

5. A compound of formula (I) as claimed in claim 1 wherein $R^a$ is hydrogen.

6. A compound of formula (I) as claimed in claim 1 wherein $R^b$ is hydrogen or methyl.

7. A compound of formula (I) as claimed in claim 1 wherein $R^c$ is hydrogen.

8. A compound of formula (I) as claimed in claim 1 wherein $R^d$ is hydrogen, hydroxy or $C_{1-4}$ alkyl.

9. A compound of formula (I) as claimed in claim 1 wherein Z is $CH_2$, $CH_2CH_2$, $CHCH_3$ or $CHOH$.

10. A compound of formula (I) as claimed in claim 1 wherein $R^2$ is phenyl or heterocyclyl optionally substituted by halogen, cyano, nitro, hydroxy, $NR^7R^8$, $C_{1-6}$ alkyl (optionally substituted with halogen), $C_{1-6}$ alkoxy (optionally substituted with halogen), $S(O)_p($ $C_{1-6}$ alkyl), $S(O)_rCF_3$ or $S(O)_2NR^{14}R^{15}$; p and r are, independently, 0, 1 or 2; and $R^7$, $R^8$, $R^{14}$ and $R^{15}$ are, independently, hydrogen, $C_{1-6}$ alkyl (optionally substituted by halogen, hydroxy or $C_{3-10}$ cycloalkyl), $CH_2$ ($C_{2-5}$ alkenyl), phenyl (itself optionally substituted by halogen, hydroxy, nitro, $NH_2$, $NH(C_{1-4}$ alkyl), $N(C_{1-4}$ alkyl)$_2$, $S(O)_2(C_{1-4}$ alkyl), $S(O)_2NH_2$, $S(O)_2NH(C_{1-4}$ alkyl), $S(O)_2N(C_{1-4}$ alkyl)$_2$ (and these alkyl groups optionally join to form a ring as described for $R^7$ and $R^8$ below), cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$ (and these alkyl groups optionally join to form a ring as described for $R^7$ and $R^8$ below), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$) or heterocyclyl (itself optionally substituted by halogen, hydroxy, nitro, $NH_2$, $NH(C_{1-4}$ alkyl), $N(C_{1-4}$ alkyl)$_2$, $S(O)_2(C_{1-4}$ alkyl), $S(O)_2NH_2$, $S(O)_2NH(C_{1-4}$ alkyl), $S(O)_2N(C_{1-4}$ alkyl)$_2$ (and these alkyl groups optionally join to form a ring as described for $R^7$ and $R^8$ below), cyano, $C_{1-4}$ alkyl, $C_{1-4}$ alkoxy, $C(O)NH_2$, $C(O)NH(C_{1-4}$ alkyl), $C(O)N(C_{1-4}$ alkyl)$_2$ (and these alkyl groups optionally join to form a ring as described for $R^7$ and $R^8$ below), $CO_2H$, $CO_2(C_{1-4}$ alkyl), $NHC(O)(C_{1-4}$ alkyl), $NHS(O)_2(C_{1-4}$ alkyl), $C(O)(C_{1-4}$ alkyl), $CF_3$ or $OCF_3$); or alternatively $NR^7R^8$ or $NR^{14}R^{15}$, independently, form a 4-7 membered heterocyclic ring, azetidine, pyrrolidine, piperidine, azepine, morpholine or piperazine, the latter optionally substituted by $C_{1-4}$ alkyl on the distal nitrogen.

11. A compound of formula (I) as claimed in claim 1 wherein $R^2$ is phenyl or heterocyclyl optionally substituted by halogen, cyano, hydroxy, $C_{1-4}$ alkyl, $C_{1-4}$ haloalkyl or $C_{1-4}$ alkoxy.

12. A compound of formula (I) as claimed in claim 1 wherein heterocyclyl is indolyl, imidazolyl, thienyl or pyridinyl.

13. A process for preparing a compound of formula (I) as claimed in claim 1 comprising:
   a. reacting a compound of formula (II):

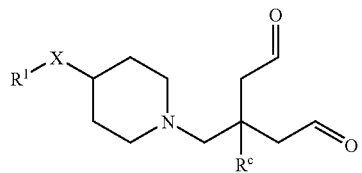

with a compound of formula (III):

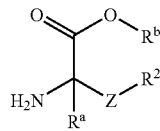

in the presence of $NaBH(OAc)_3$ or $NaBH_3(CN)$ in a suitable solvent at a suitable temperature;
   b. when $R^b$ is not hydrogen, reacting a compound of formula (II) with a compound of formula (III), where $R^b$ is not hydrogen, in the presence of $NaBH(OAc)_3$ and a suitable base in a suitable solvent at a suitable temperature;
   c. when $R^a$ represents H, reacting a compound of formula (IX):

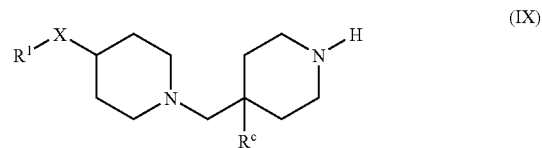

with a compound of formula (X):

wherein L is a suitable leaving group, in a suitable solvent, at a temperature in the range 0° C. to 30° C., in the presence of a base; or,
   d. when $R^a$ represents H, hydrolysing a compound of formula (XIV):

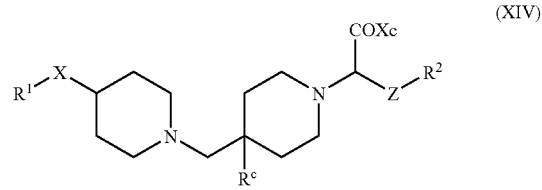

wherein Xc is a chiral auxiliary, in a suitable solvent, at a temperature between 10° C. and reflux of the solvent.

14. A pharmaceutical composition which comprises a compound of the formula (I), or a pharmaceutically acceptable salt thereof as claimed in claim 1, and a pharmaceutically acceptable adjuvant, diluent or carrier.

15. A compound of formula (I) as claimed in claim 2 wherein $R^1$ is phenyl optionally substituted with halogen, cyano, $C_{1-4}$ alkyl or $C_{1-4}$ alkoxy.

16. A compound of formula (I) as claimed in claim 2 wherein $R^a$ is hydrogen.

17. A compound of formula (I) as claimed in claim 2 wherein $R^b$ is hydrogen or methyl.

18. A compound of formula (I) as claimed in claim 2 wherein $R^c$ is hydrogen.

19. A compound of formula (I) as claimed in claim 2 wherein $R^d$ is hydrogen, hydroxy or $C_{1-4}$ alkyl.

* * * * *

UNITED STATES PATENT AND TRADEMARK OFFICE
CERTIFICATE OF CORRECTION

PATENT NO. : 7,495,013 B2
APPLICATION NO. : 10/551493
DATED : February 24, 2009
INVENTOR(S) : Moya Caffrey It is certified that error appears in the above-identified patent and that said Letters Patent is hereby corrected as shown below:

<u>First Page, Column 1</u>
Insert immediately before "(51) Int. Cl.":

-- (30)   Foreign Application Priority Date
          April 1, 2003 (SE) .................. 0300957-8 --.

<u>Column 38, Line 67</u>
Delete "phenyl($C_{1-4}$alkyl," insert -- phenyl($C_{1-4}$)alkyl, --.

<u>Columns 38-39, Lines 67 and 1</u>
Delete "phenyl($C_{1-4}$alkoxy," insert -- phenyl($C_{1-4}$)alkoxy, --.

<u>Column 39, Line 1</u>
Delete "heterocyclyl($C_{1-4}$alkyl," insert -- heterocyclyl($C_{1-4}$)alkyl, --.

<u>Column 39, Line 16 (approx.)</u>
Delete "$R^{17}$".

<u>Column 40, Line 25 (approx.)</u>
Delete "$R^{17}$".

<u>Column 40, Line 25 (approx.)</u>
Delete "$R^{11}$," and insert -- $R^{11}$, --.

UNITED STATES PATENT AND TRADEMARK OFFICE
CERTIFICATE OF CORRECTION

PATENT NO. : 7,495,013 B2
APPLICATION NO. : 10/551493
DATED : February 24, 2009
INVENTOR(S) : Moya Caffrey It is certified that error appears in the above-identified patent and that said Letters Patent is hereby corrected as shown below:

Column 42, Line 2
Delete "(TX):" and insert -- (IX): --.

Signed and Sealed this

Twelfth Day of May, 2009

JOHN DOLL
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 7,495,013 B2 | Page 1 of 1 |
| APPLICATION NO. | : 10/551493 | |
| DATED | : February 24, 2009 | |
| INVENTOR(S) | : Caffrey et al. | |

It is certified that error appears in the above-identified patent and that said Letters Patent is hereby corrected as shown below:

On the cover page,

[*] Notice:   Subject to any disclaimer, the term of this patent is extended or adjusted under 35 USC 154(b) by 530 days Delete the phrase "by 530 days" and insert -- by 678 days --

Signed and Sealed this

Sixth Day of April, 2010

David J. Kappos
*Director of the United States Patent and Trademark Office*